(12) United States Patent
Fahey

(10) Patent No.: US 9,302,104 B2
(45) Date of Patent: *Apr. 5, 2016

(54) DEVICES, SYSTEMS, AND METHODS FOR AUTOMATED OPTIMIZATION OF ENERGY DELIVERY

(71) Applicant: NIVEUS MEDICAL, INC., Redwood City, CA (US)

(72) Inventor: Brian J. Fahey, Palo Alto, CA (US)

(73) Assignee: NIVEUS MEDICAL, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/532,595

(22) Filed: Nov. 4, 2014

(65) Prior Publication Data

US 2015/0127064 A1 May 7, 2015

Related U.S. Application Data

(60) Division of application No. 13/647,249, filed on Oct. 8, 2012, now Pat. No. 8,892,210, which is a continuation-in-part of application No. 12/497,230, filed on Jul. 2, 2009, now Pat. No. 8,285,381.

(60) Provisional application No. 61/133,777, filed on Jul. 2, 2008, provisional application No. 61/189,558, filed on Aug. 19, 2008, provisional application No. 61/190,602, filed on Aug. 29, 2008, provisional application No. 61/201,877, filed on Dec. 15, 2008, provisional application No. 61/544,113, filed on Oct. 6, 2011.

(51) Int. Cl.
*A61N 1/00* (2006.01)
*A61N 1/36* (2006.01)
(Continued)

(52) U.S. Cl.
CPC ............ *A61N 1/36003* (2013.01); *A61B 19/54* (2013.01); *A61H 39/002* (2013.01); *A61N 1/0492* (2013.01); *A61N 1/36014* (2013.01); *A61B 5/0492* (2013.01); *A61B 5/4523* (2013.01); *A61B 5/4585* (2013.01); *A61B 5/4836* (2013.01); *A61B 5/6828* (2013.01); *A61B 5/6841* (2013.01); *A61B 2019/5404* (2013.01); *A61H 2201/165* (2013.01); *A61H 2201/5005* (2013.01); *A61H 2201/5015* (2013.01); *A61H 2201/5061* (2013.01); *A61H 2201/5084* (2013.01); *A61H 2201/5092* (2013.01); *A61H 2201/5097* (2013.01); *A61H 2205/10* (2013.01);
(Continued)

(58) Field of Classification Search
USPC ....................................................... 607/48–50
See application file for complete search history.

(56) References Cited

U.S. PATENT DOCUMENTS

| 4,108,146 A | 8/1978 | Golden |
| 4,390,023 A | 6/1983 | Rise |

(Continued)

FOREIGN PATENT DOCUMENTS

| FR | 2596654 A | 10/1987 |
| JP | 2001-025510 | 1/2001 |

(Continued)

OTHER PUBLICATIONS

Baker et al.; Effects of waveform on comfort during neuromuscular electrical stimulation; Clin Ortho Res; vol. 233; pp. 75-85; Aug. 1988.

(Continued)

*Primary Examiner* — Nicole F Lavert
(74) *Attorney, Agent, or Firm* — Shay Glenn LLP

(57) ABSTRACT

Devices, systems, and methods for automated optimization of muscle stimulation energy. In some embodiments the disclosure optimizes stimulation parameters and/or stimulation location.

25 Claims, 10 Drawing Sheets

(51) Int. Cl.
*A61H 39/00* (2006.01)
*A61B 19/00* (2006.01)
*A61B 5/0492* (2006.01)
*A61B 5/00* (2006.01)
*A61N 1/04* (2006.01)

(52) U.S. Cl.
CPC ..... *A61H2205/104* (2013.01); *A61H 2230/045* (2013.01); *A61H 2230/655* (2013.01); *A61N 1/0452* (2013.01); *A61N 1/0476* (2013.01)

(56) References Cited

U.S. PATENT DOCUMENTS

| | | | |
|---|---|---|---|
| 4,480,830 A | 11/1984 | Petrofsky et al. | |
| 4,580,569 A | 4/1986 | Petrofsky | |
| 4,619,266 A | 10/1986 | Hodgson | |
| 4,736,752 A | 4/1988 | Munck et al. | |
| 4,805,636 A | 2/1989 | Barry et al. | |
| 4,811,742 A | 3/1989 | Hassel et al. | |
| 4,838,272 A | 6/1989 | Lieber | |
| 4,867,166 A | 9/1989 | Axelgaard et al. | |
| 4,962,761 A | 10/1990 | Golden | |
| 4,969,468 A | 11/1990 | Byers et al. | |
| 5,010,896 A | 4/1991 | Westbrook | |
| 5,016,635 A | 5/1991 | Graupe | |
| 5,070,873 A | 12/1991 | Graupe et al. | |
| 5,097,828 A | 3/1992 | Deutsch | |
| 5,314,423 A | 5/1994 | Seney | |
| 5,336,255 A | 8/1994 | Kanare et al. | |
| 5,397,338 A | 3/1995 | Grey et al. | |
| 5,507,788 A | 4/1996 | Lieber | |
| 5,549,656 A | 8/1996 | Reiss | |
| 5,674,262 A | 10/1997 | Tumey | |
| 5,702,323 A | 12/1997 | Poulton | |
| 5,702,429 A | 12/1997 | King | |
| 5,843,152 A | 12/1998 | Tu et al. | |
| 5,871,526 A | 2/1999 | Gibbs et al. | |
| 5,902,328 A | 5/1999 | LaFontaine et al. | |
| 6,216,704 B1 | 4/2001 | Ingle et al. | |
| 6,266,558 B1 | 7/2001 | Gozani et al. | |
| 6,301,500 B1 | 10/2001 | Van Herk et al. | |
| 6,324,432 B1 | 11/2001 | Rigaux et al. | |
| 6,341,237 B1 | 1/2002 | Hurtado | |
| 6,350,276 B1 | 2/2002 | Knowlton | |
| 6,480,731 B1 | 11/2002 | DeLuca et al. | |
| 6,505,078 B1 | 1/2003 | King et al. | |
| 6,567,696 B2 | 5/2003 | Voznesensky et al. | |
| 6,829,510 B2 | 12/2004 | Nathan et al. | |
| 6,840,955 B2 | 1/2005 | Ein | |
| 6,944,503 B2 | 9/2005 | Crowe et al. | |
| 7,146,220 B2 | 12/2006 | Dar et al. | |
| 7,172,564 B2 | 2/2007 | Bosco | |
| 7,204,832 B2 | 4/2007 | Altshuler et al. | |
| 7,221,980 B2 | 5/2007 | Kotlik et al. | |
| 7,236,832 B2 | 6/2007 | Hemmerling et al. | |
| 7,257,448 B2 | 8/2007 | Crowe et al. | |
| 7,276,058 B2 | 10/2007 | Altshuler et al. | |
| 7,473,251 B2 | 1/2009 | Knowlton et al. | |
| 7,483,738 B2 | 1/2009 | Tamarkin et al. | |
| 7,499,746 B2 | 3/2009 | Buhlmann et al. | |
| 8,216,218 B2 | 7/2012 | Burns et al. | |
| 8,265,763 B2 | 9/2012 | Fahey | |
| 8,285,381 B2 | 10/2012 | Fahey | |
| 8,433,403 B2 | 4/2013 | Fahey | |
| 8,588,901 B2 | 11/2013 | Fahey | |
| 8,676,332 B2 | 3/2014 | Fahey | |
| 8,892,210 B2 | 11/2014 | Fahey | |
| 2002/0049483 A1 | 4/2002 | Knowlton | |
| 2002/0143365 A1 | 10/2002 | Herbst | |
| 2002/0151951 A1 | 10/2002 | Axelgaard et al. | |
| 2003/0229385 A1 | 12/2003 | Elkins | |
| 2004/0044384 A1 | 3/2004 | Leber et al. | |
| 2004/0173220 A1 | 9/2004 | Harry et al. | |
| 2004/0254624 A1 | 12/2004 | Johnson | |
| 2005/0288730 A1 | 12/2005 | Deem et al. | |
| 2006/0142816 A1 | 6/2006 | Fruitman et al. | |
| 2007/0106343 A1 | 5/2007 | Monogue et al. | |
| 2007/0178579 A1 | 8/2007 | Brown et al. | |
| 2007/0203435 A1 | 8/2007 | Novak | |
| 2008/0045775 A1* | 2/2008 | Lozano | 600/12 |
| 2008/0161883 A1 | 7/2008 | Conor | |
| 2008/0195010 A1 | 8/2008 | Lai et al. | |
| 2008/0208288 A1 | 8/2008 | Gesotti | |
| 2009/0012436 A1 | 1/2009 | Lanferman et al. | |
| 2010/0081963 A1 | 4/2010 | Gilhuly | |
| 2011/0082517 A1 | 4/2011 | Brezel et al. | |
| 2014/0005759 A1 | 1/2014 | Fahey et al. | |
| 2014/0058477 A1 | 2/2014 | Fahey | |

FOREIGN PATENT DOCUMENTS

| | | |
|---|---|---|
| JP | 2002-052000 | 2/2002 |
| JP | 2006510431 | 3/2006 |
| KR | 10-866543 B | 11/2008 |
| WO | WO 01/52759 A1 | 7/2001 |
| WO | WO 03/086217 A1 | 10/2003 |
| WO | WO 2004/089185 A2 | 10/2004 |
| WO | WO 2004/098703 A2 | 11/2004 |
| WO | WO 2005/075018 A1 | 8/2005 |
| WO | WO 2005/105203 A1 | 11/2005 |
| WO | WO 2007/017778 A2 | 2/2007 |
| WO | WO 2007/041540 A1 | 4/2007 |
| WO | WO 2007/046886 A1 | 4/2007 |
| WO | WO 2008/032282 A2 | 3/2008 |
| WO | WO 2008/034607 A1 | 3/2008 |
| WO | WO 2008/075250 A1 | 6/2008 |
| WO | WO 2008/116232 A1 | 9/2008 |
| WO | WO 2009/009661 A1 | 1/2009 |

OTHER PUBLICATIONS

Bennie et al.; Toward the optimal waveform for electrical stimulation of human muscle; Eur J Appl Physiol; vol. 88; pp. 13-19; Nov. 2002.

Lacey et al.; Reductions in the amount of time spent in direct patient care by staff nurses in North Carolina; North Carolina Center for Nursing; Aug. 2002.

Lyons et al.; An investigation of the effect of electrode size and electrode location on comfort during stimulation of the gastrocnemius muscle; Medical Engineering & Physics; vol. 26; pp. 873-878; Dec. 2004.

Miklavcic et al.; Electrical Properties of Tissues; Wiley Encyclopedia of Biomedical Engineering; (year of publication is sufficiently earlier than the effective U.S. filing date and any foreign priority date) 2006.

Morris, Peter E.; Moving our critically ill patients: mobility barriers and benefits; Critical Care Clinics; vol. 23; pp. 1-20; Jan. 2007.

Petrofsky et al.; Estimation of the distribution of intramuscular current during electrical stimulation of the quadriceps muscle; Eur J Appl Physiol; vol. 103(3); pp. 265-273; Jun. 2008.

Prausnitz, Mark R.; The effects of electrical current applied to skin: a review for transdermal drug delivery; Advanced Drug Delivery Reviews; vol. 18; pp. 395-425; Feb. 8, 1996.

Rafolt et al.; Dynamic force responses in electrically stimulated triceps surae muscles: effects of fatigue and temperature; Artificial Organs; vol. 23; No. 5; pp. 436-439; May 1999.

Solomon et al.; The effects of TENS, heat, and cold on the pain thresholds induced by mechanical pressure in healthy volunteers; Neuromodulation; vol. 6; No. 2; pp. 102-107; Apr. 2003.

Stecker et al.; Mechanisms of electrode induced injury. Part 1: theory; Am. J. END Tech.; vol. 46; pp. 315-342; Dec. 2006.

Snyder-Mackler et al.; Use of electrical stimulation to enhance recovery of quadriceps femoris muscle force production in patients following anterior cruciate ligament reconstruction; Phys Ther.; 74(10):901-7; Oct. 1994.

Suganuma et al.; Measurement of Tension of tendon tissue based on electrical impedance; J. Ortho Science; vol. 9; pp. 302-309; (year of publication is sufficiently earlier than the effective U.S. filing date and any foreign priority date) 2004.

Zanotti et al.; Peripheral muscle strength training in bed-bound patients with COPD receiving mechanical ventilation: effect of electrical stimulation; Chest; vol. 124; No. 1; pp. 292-296; Jul. 2003.

\* cited by examiner

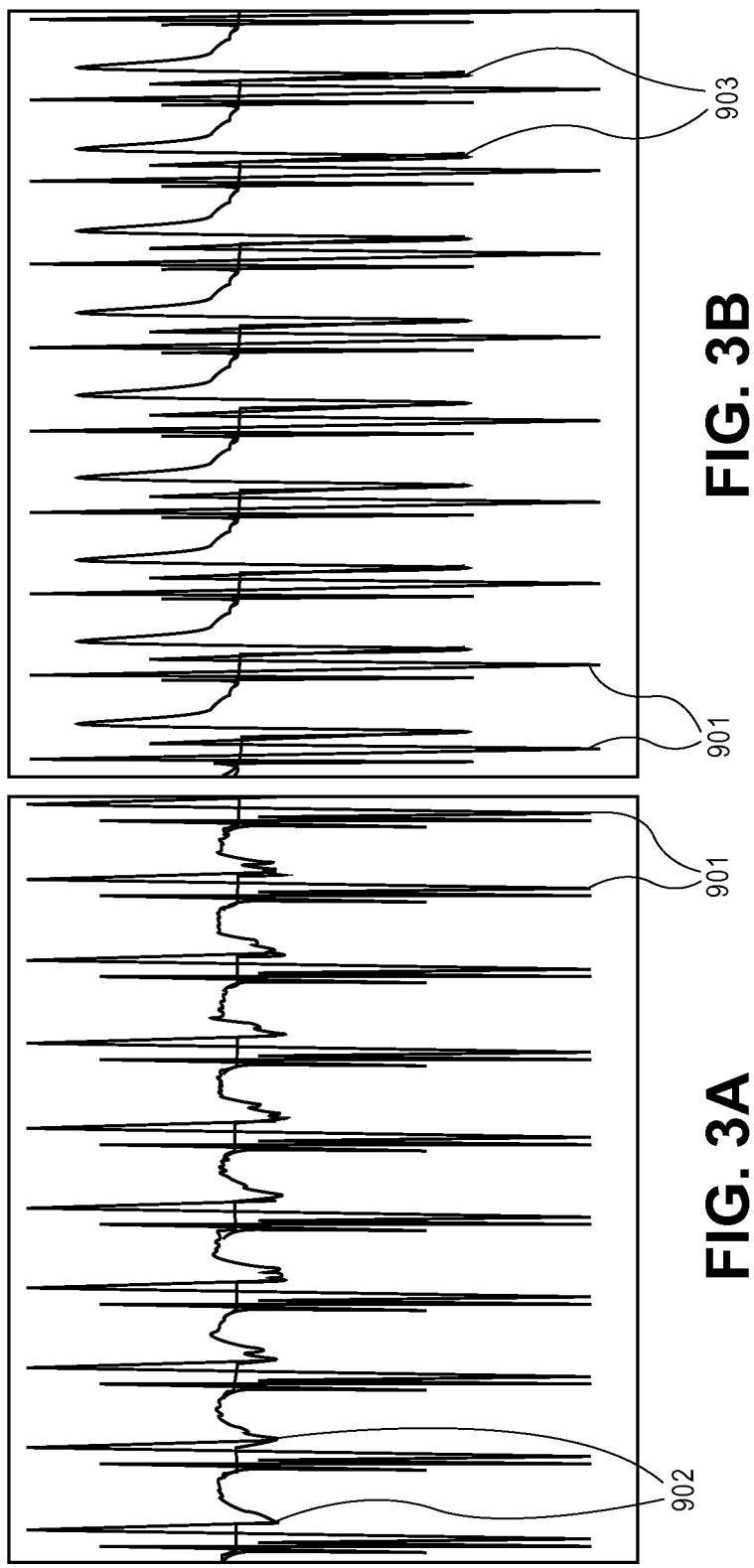

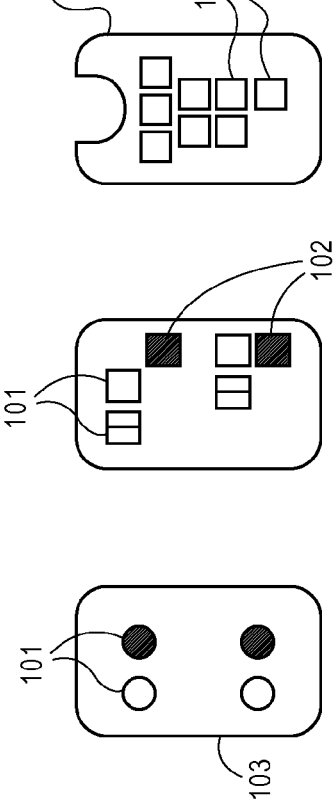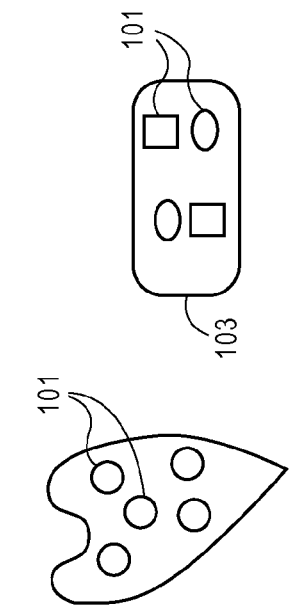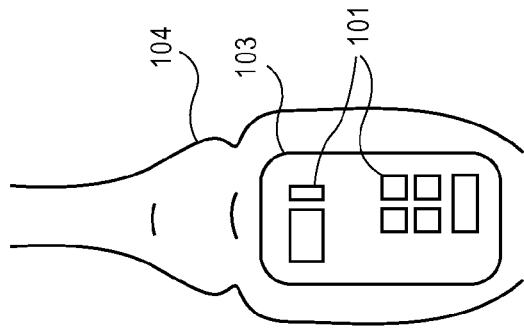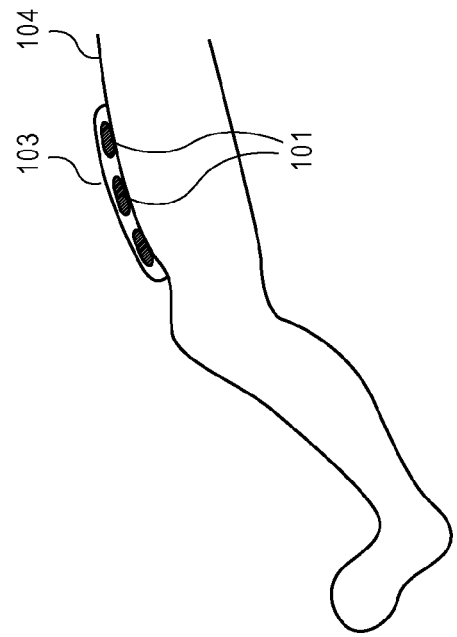

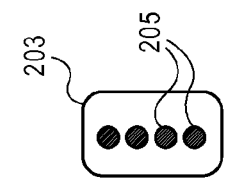
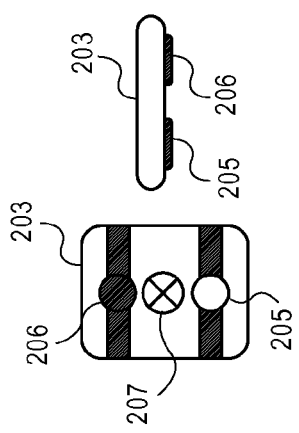
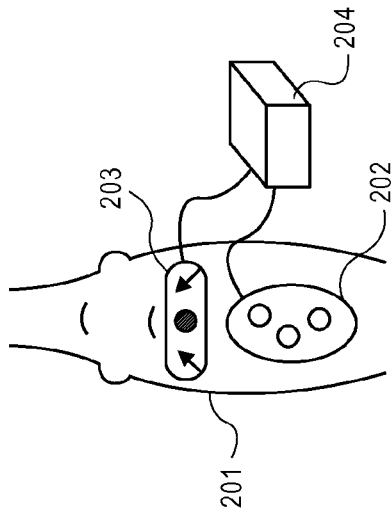
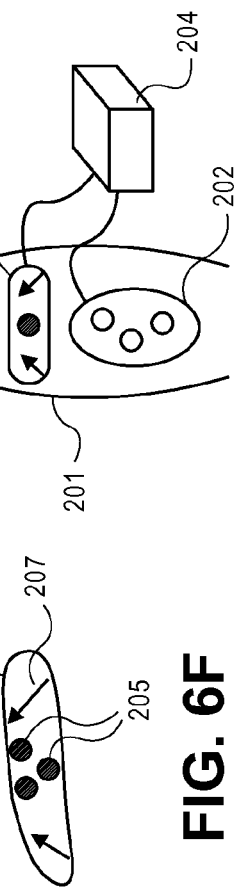
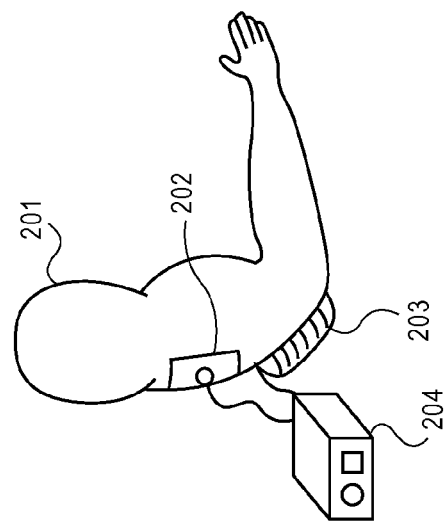
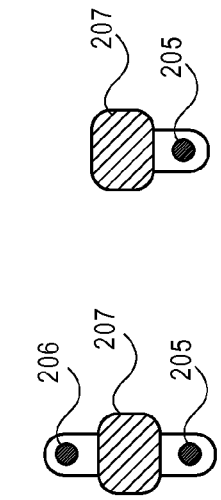

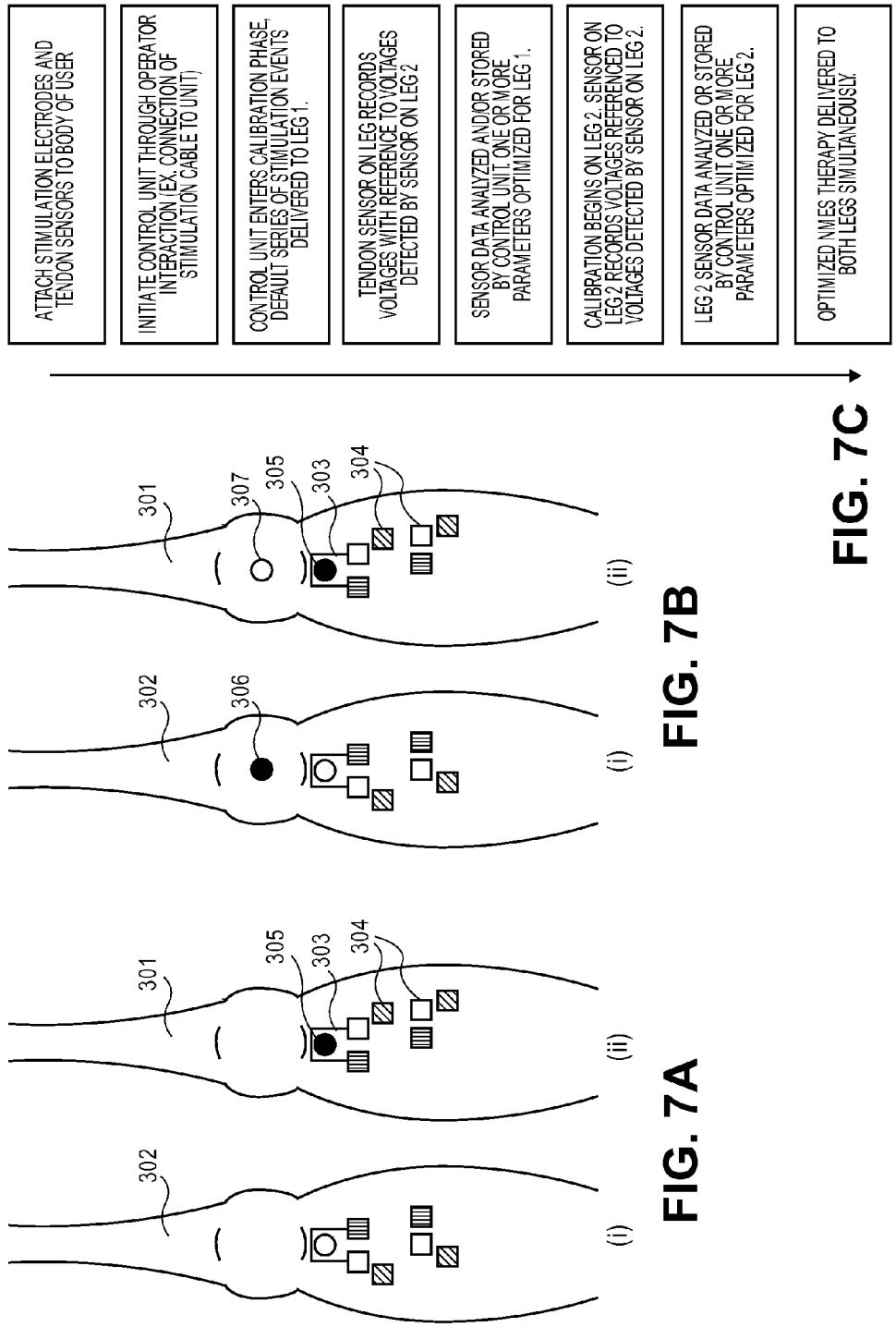

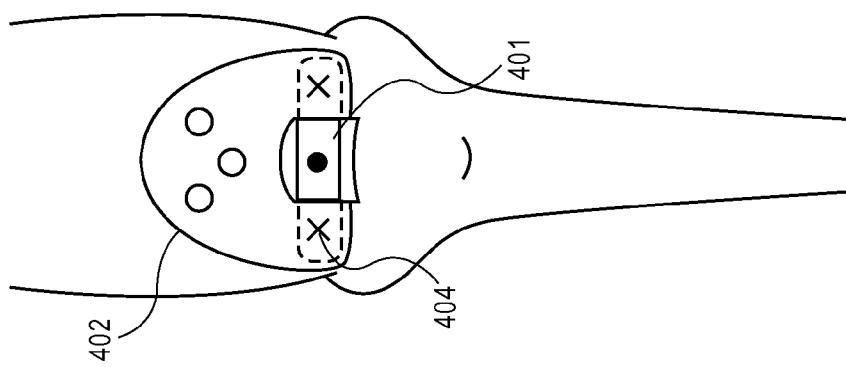
FIG. 8D
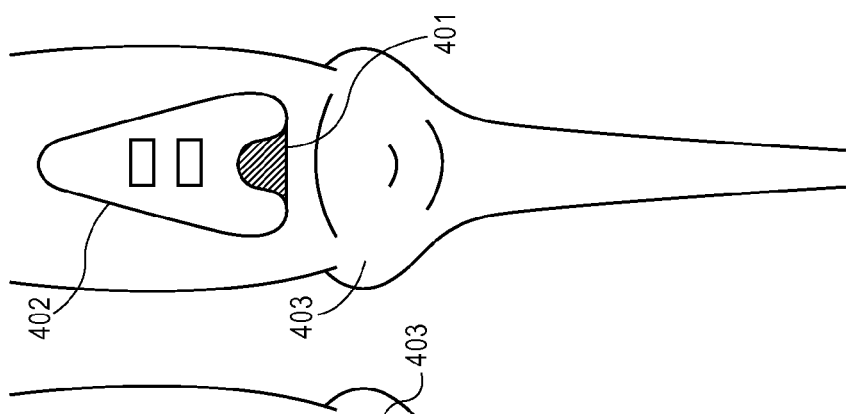
FIG. 8C
FIG. 8B
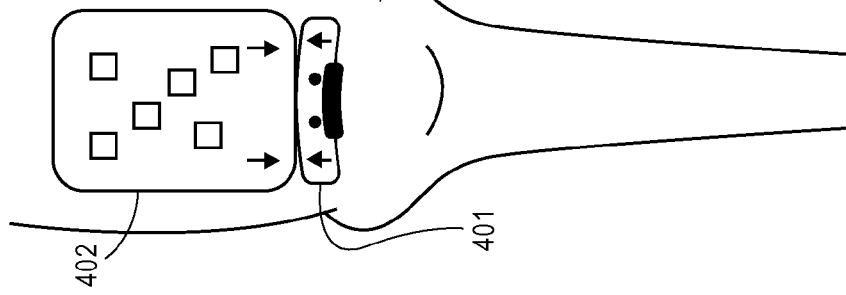
FIG. 8A
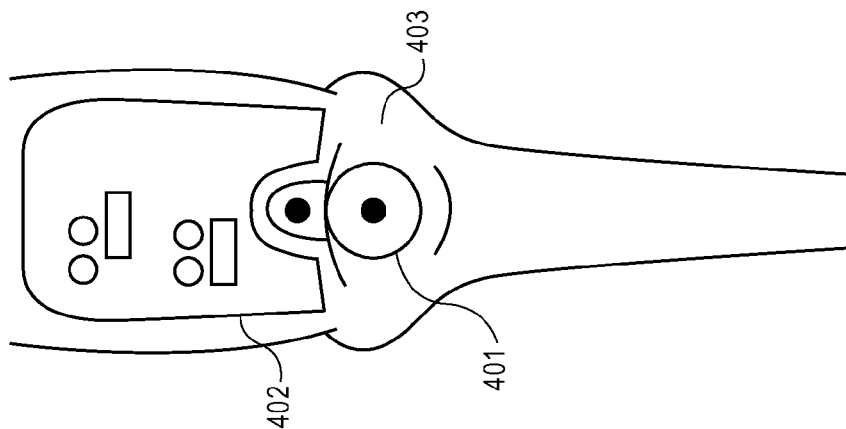

DEVICES, SYSTEMS, AND METHODS FOR AUTOMATED OPTIMIZATION OF ENERGY DELIVERY

CROSS REFERENCE TO RELATED APPLICATIONS

This application is a division of U.S. application Ser. No. 13/647,249, filed Oct. 8, 2012, now U.S. Pat. No. 8,892,210, which is a continuation-in-part of U.S. application Ser. No. 12/497,230, filed Jul. 2, 2009, now U.S. Pat. No. 8,285,381, which claims priority to U.S. Prov. App. No. 61/133,777, filed Jul. 2, 2008, U.S. Prov. App. No. 61/189,558, filed Aug. 19, 2008, U.S. Prov. App. No. 61/190,602, filed Aug. 29, 2008, and U.S. Prov. App. No. 61/201,877, filed Dec. 15, 2008; all of which are incorporated herein by reference.

Application Ser. No. 13/647,249 also claims priority to U.S. Prov. App. No. 61/544,113, filed Oct. 6, 2011, incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Acutely or chronically ill persons may be immobilized during the course of their illness. This state of immobility leads to disuse of skeletal muscles, which in turn leads to immediate and progressive atrophy that results in profound muscle weakness over time. When the illness improves and the person is no longer immobile, the muscle weakness remains. Typically, a long rehabilitation period is required to recover function lost during a relatively short period of immobility. Prevention of immobility-based debilitation is challenging in the case of patients who are physically or mentally unable to participate in active exercise, for example critically-ill patients in the intensive care unit (ICU) of a hospital. These patients are often sedated or otherwise non-participative, eliminating voluntary exercise and the most beneficial forms of Physical Therapy from consideration. As a result, in most ICUs in the United States, literally nothing is done to prevent the onset of immobility-based debilitation and profound weakness.

Neuromuscular electrical stimulation ("NMES") (also referred to as powered muscle stimulation, functional muscle stimulation, electrical muscle stimulation, and other terms) is a technology capable of activating a person's muscles involuntarily and non-invasively. However, despite recent studies that have both hypothesized and proven the benefit of NMES for use with bed-bound patients (e.g., see Zanotti et al, Chest 124:292-296, 2003 and Morris et al., Critical Care Clinics, 23:1-20, 2007, both incorporated herein by reference), it is not widely deployed in ICUs throughout the U.S. This is largely related to the labor-intensive nature of delivering effective NMES therapy. In clinical settings, labor-intensive protocols often inhibit the adoption of therapeutic treatments. This is particularly true in the ICU setting, where the primary care giver is an ICU nurse who spends his or her time split between patient care and other duties, such as charting. Most often, critical care nurses have their time fully committed, and cannot take on a new patient care activity without discarding another. Because debilitation-prevention is not vital to a critically ill person's immediate survival, NMES delivery would need to be very time-efficient in order for it to be implemented in the ICU setting. As virtually no ICU nurses are trained to deliver NMES, time-efficient delivery of this therapy by nursing staff in its current state-of-the-art form is not feasible. Given skyrocketing health-care costs, many institutions cannot afford or cannot justify hiring additional help, especially well-compensated advanced operators trained in delivering NMES.

One complicating factor that makes NMES difficult to deliver in a time-efficient manner is that each person responds differently to applied energy. Factors such as body-fat percentage, baseline muscle mass, and degree of skin hydration will all contribute to how well a person's muscles respond to a given energy intensity. Thus, it is often required to adjust stimulation parameters, such as pulse length, amplitude of applied voltage/current, and pulse-repetition frequency, on a case-by-case basis to ensure that a person receives effective therapy that is both safe and well-tolerated. Doing this task successfully is challenging. For example, it is well known that a stimulation energy intensity that simply produces visible muscle contraction is typically too low of an energy intensity for ideal therapeutic benefit. As illustrated by Snyder-Mackler and colleagues (*Physical Therapy*, Vol. 70, No. 10, 1994—incorporated herein by reference), stronger contractions often lead to better therapeutic outcomes than weaker contractions. Since it can be very difficult to visually differentiate varying degrees of moderate-to-strong muscle contraction (as opposed to binary assessments of contraction/no contraction) accurately, energy intensity adjustment is a tedious process and is often done sub-optimally. Even with a trained operator, parameter adjustment is typically an iterative and time-consuming process and still leads to sub-optimal results. This problem is exacerbated in the ICU, where untrained operators (nurses) would be required to make these assessments absent of any verbal feedback from non-communicative patients.

There are also safety issues related to the choice of stimulation parameters that may be operator-controlled. Current density, a function of injected charge, must be carefully controlled to avoid burns, nerve injury, and other potential complications (as detailed by Prausnitz Advanced Drug Delivery Reviews 18:395-425,2006 and Stecker et al Am J END Tech., 43:315-342, 2006, both of which are incorporated herein by reference). Thus, it is important not to grossly overestimate a person's energy intensity requirements in an attempt to maximize therapeutic benefit.

Further complications are related to the fact that ideal placement of stimulation electrodes may differ considerably from person-to-person. During stimulation of large muscle groups (ex. gluteals, quadriceps), electrode placement differences of less than 1 cm can reduce stimulation effectiveness by 50% or more. Precise electrode placement is required if muscles are to be activated effectively in a manner such that the person receiving therapy experiences minimal discomfort. Current methods to determine electrode placement involve initial estimations based upon anatomical markers, followed by iterative trial-and-error based adjustments based upon an observed muscle response. As with the required stimulation parameter adjustments noted above, finding suitable electrode locations proximal to muscle motor points is often labor-intensive endeavor.

The shortcomings of existing NMES technologies with regard to their ease-of use (particularly when used with challenging patients—such as the obese, elderly, and/or edematous) are widely recognized. To this end, several solutions have been proposed that include some type of sensor coupled to the stimulation pulse generator via feedback mechanisms.

However, sensor-based solutions described in the prior art to date often function poorly, are costly and cumbersome to implement, and/or are inadequate for certain patient care scenarios. For example, EMG-based monitoring of muscle response during NMES is ineffective, because an EMG signal (amplitude on the order of mV) must be recorded in the same region and at the same time an NMES signal is delivered (amplitudes of up to ~50V). This is especially true in scenarios where needle-based EMG electrodes are not used— i.e., situations where patient comfort, infection control, skin integrity management, or other concerns make their use inconvenient or unadvisable. Advanced signal processing algorithms or sophisticated filters may help improve signal-to-noise ratio, but in most situations these EMG signals are not adequate for successful optimization of NMES. As another illustrative example, accelerometer-based sensor systems have been proposed in the prior art as a way to self-optimize a muscle stimulator. However, accelerometers, strain gauges, and other displacement/strain/motion-based sensors fail in many clinical settings. For instance, in the ICU, sedated patients lie in bed with arms and legs fully or nearly-fully extended. Thus, contraction of important muscle groups such as the quadriceps and triceps produce little to no anatomical movement or acceleration, often resulting in unreliable accelerometer measurements of poor quality.

Existing NMES devices and technologies that are disclosed in the prior art do not include mechanisms to sufficiently improve ease of use and reduce therapy delivery time in high-demand clinical settings and with non-interactive patients. Further, previously-disclosed devices, systems, and methods of NMES do not teach robust sensor systems that are both robust enough and simple enough for use in these clinical environments. As a result, a proven-effective technology is not implemented in a large patient group that could benefit substantially from it.

A need still remains for devices, systems, and methods of use that can reduce implementation times for NMES by providing automated adjustment of stimulation parameters, energy delivery locations, or both. A secondary need also remains for devices, systems, and methods that improve the quality of NMES therapy by ensuring that optimal stimulation parameters and/or energy delivery locations are used on a per-person basis.

SUMMARY OF THE DISCLOSURE

The disclosure generally described devices, systems, and methods for automated optimization of energy delivery to human or animal tissue. Though this disclosure uses the modality of NMES as an illustrative example, with minor modifications the devices, systems, and methods described herein may be applied with utility to other energy-delivery therapies, such as TENS or RF or microwave ablative therapies, as well. An objective of the presently-disclosed devices, systems, and methods is to simultaneously increase the effectiveness of energy delivery by selecting optimum stimulation parameters and energy delivery locations for use and to decrease the operator-time required in order to deliver a safe and effective NMES therapy. In preferable embodiments of the presently-disclosed devices, systems, and methods, this multi-faceted improvement to NMES state-of-the-art is achieved through the use of an inventive sensor system that is functionally superior to NMES sensor systems described previously. Some implementations involve the use of inventive tendon-based sensors that examine anatomical properties indicative of the degree of muscle contraction. Preferable embodiments will also include newly-developed signal processing steps that examine signal characteristics and sensor data patterns that have not been previously recognized.

In some preferable embodiments of the devices, systems, and methods, at least one sensor capable of extracting electrical signals from the surface of the body (as one example, a sensor similar to an EKG sensor) is placed on or around the muscle region that is targeted for NMES therapy. In some cases, this may be the region of the tendon that is mechanically-coupled to the targeted muscle. For example, if quadriceps muscles are stimulated to contract, one suitable location for the sensor(s) would be on the surface of the skin in the region directly over the quadriceps tendon. Tendons are bands of tough fibrous tissue that are composed mostly of collagen fibers, and do not produce electrical activity during muscle contraction in the same way that muscle tissues do. As a result, a large portion of electrical activity detected by sensors located near tendons originate from the energy source used to stimulate muscle contraction. Accordingly, these electrical signals travel along and/or around the tendon before reaching the skin surface, where they are detected by the sensors.

In some embodiments, non-electrical-based tendon sensors are utilized to measure changes in tendon tension, geometry, and/or electrical impedance. For example, an indenter-based system or non-contact imaging technique (for example, ultrasound-based elastography) may be used to assess tissue stiffness in the anatomic region of the tendon, which will serve as a suitable proxy to measure tendon tension (as non-compressible elastic materials such as tissue may stiffen under mechanical strain). Another example uses a magnetic or inductive sensor to detect electrical impedance changes non-invasively without depending on the direct extraction of electrical signals from the body.

In some implementations of a preferable embodiment, electrical sensors are not placed in tendon regions and/or are not dependent upon tendon properties to function properly as part of the systems or methods. In these implementations sensors function similarly to as described above; electrical energy delivered to the body by an external source is measured by sensors located outside of the area of delivery. Signals measured by sensors are reflective of the degree of muscle contraction induced and thus information from sensors is used to optimize one or more parameters related to NMES therapy.

The benefits to using the presently-described approaches over previously described sensors such as EMG, accelerometer, strain gauge, etc., are numerous. For instance, the disclosed systems and methods of use overcome the EMG signal-to-noise ratio issues described in the background section by capturing and processing an inventive (and strong) electrical signal in a region with little to no unwanted electrical noise. Additional benefits of the sensor systems are seen for use with ICU patients, who often suffer from tissue edema (swelling) that inhibits the use of surface electrodes (including EMG electrodes) over soft tissue areas. As the sensors, such as tendon sensors, are typically best-placed near bony prominences (e.g., knee, elbow, etc.), the effect of edema on signal quality is typically minimal.

Preferable embodiments of the methods disclosed include several steps that will allow for increases in the effectiveness of NMES by selecting optimum parameters and energy delivery locations for use coupled with decreases in the operator-time required in order to deliver safe, effective NMES therapy. In a preferable implementation of the methods, a first step involves placing one or more pairs or groups of electrodes on the surface of the skin in the vicinity of the muscle it is desired to stimulate. A later step involves placing one or more sensors (for example, tendon sensors) on a sensing location that is different and away from the region of stimulation. A third step involves automatically (potentially without user or operator interaction) optimizing at least one stimulation pulse parameter and/or energy delivery locations using information sensed from the sensor(s). A variation of this embodiment involves an additional step where a second sensor, acting as a ground that collects a reference signal, is placed on the body in a region remote to NMES delivery.

In a preferable embodiment of a stimulation system and method, a stimulation control unit sequentially steps through a series of default stimulation events. Sensor data are captured from each event and analyzed individually, as a collective ensemble of data from two or more events, or both. Hardware, software, firmware, or a combination of these tools is used to adapt stimulation based upon outcomes of analysis provided by decision-making algorithms applied to the sensor data. In one implementation, the adaptation step comprises choosing a specific pair or group of electrodes from a larger electrode array to use during NMES treatment. In a second implementation of this preferable embodiment, the adaptation step comprises altering the electrical energy intensity used or another stimulation parameter associated with NMES. A third implementation would adjust both energy delivery location and at least one stimulation pulse parameter.

The devices, systems, and methods are useful because when implemented they will enable proven therapies to be delivered time-efficiently in high demand clinical settings where therapy-delivery logistics and operator time requirements may otherwise prevent their adoption. For example, weakness and debilitation following prolonged bed rest in the ICU is a well-known problem with few proposed interventions, yet NMES is not widely-used in this setting for reasons largely related to lack of training and existing labor requirements of primary caregivers. The devices, systems, and methods are also useful because when implemented they will ensure that optimal settings are utilized during treatment settings, thus improving the therapeutic benefit of applied interventions while simultaneously improving user safety.

One aspect of the disclosure is a method of electrically stimulating muscle, comprising: applying a first electrical stimulating signal from an energy source to a muscle at a stimulation region; sensing an electrical signal in a sensing region that is away from the stimulation region when applying the first electrical stimulating signal; adjusting at least one parameter of the first electrical stimulating signal based on the sensed electrical signal; and applying a second electrical stimulating signal from the energy source to the muscle, wherein the second electrical stimulating signal comprises the at least one adjusted parameter.

In some embodiments sensing an electrical signal comprises sensing the first electrical stimulating signal, or a change that occurs in the first electrical stimulating signal between the stimulation region and the sensing region.

In some embodiments sensing an electrical signal comprises sensing an electrical signal independent of or multiplexed into the first electrical stimulating signal, or a change that occurs in the independent or multiplexed signal between the stimulation region and the sensing region.

In some embodiments the sensing step comprises sensing an electrical signal that is indicative of a state of a tendon coupled to the muscle being stimulated.

In some embodiments the first electrical stimulating energy signal has a general waveform shape and the sensing step comprises sensing an electrical signal with the same general waveform shape. The first waveform can be biphasic and the sensing step can comprise sensing the biphasic signal. The sensing step can comprise sensing a biphasic signal with the same phase distribution and approximately the same pulse width as the first waveform.

In some embodiments the method further comprises using a control unit to analyze the peak voltage amplitude of the sensed signal, and wherein adjusting the at least one parameter of the electrical stimulation energy is based on analyzing the peak voltage amplitude of the sensed energy.

In some embodiments applying a first electrical stimulating energy signal comprises positioning at least one stimulation electrode on the patient's body at the stimulation region.

In some embodiments the applying step comprises applying a first electrical stimulating signal with a first energy intensity, the method further comprising determining if the sensed electrical signal satisfies a threshold for adequate muscle contraction (for example, a threshold degree of fluctuation in sensed voltage amplitude over the period when stimulation is applied), and if so, the method further comprises delivering muscle stimulation therapy with a stimulating signal that comprises the first energy intensity. If the sensed electrical signal does not satisfy the threshold for adequate muscle contraction, the method can further include applying the second electrical stimulating signal with an second energy intensity greater than the first energy intensity, and further sensing an electrical signal during the time when the second electrical stimulating signal is applied, and determining if the second electrical stimulating signal satisfies a threshold for adequate muscle contraction.

One aspect of the disclosure is a method of electrically stimulating a muscle of a patient, comprising: sensing electrical energy delivered to a muscle from an external electrical energy source, wherein the sensing step comprises sensing electrical energy at a sensing region that is different than a stimulation region at which the electrical energy is delivered to the muscle; applying an electrical muscle stimulating signal to the muscle to stimulate the muscle, wherein at least one parameter of the electrical muscle stimulating signal is based on the sensed electrical energy delivered from the external energy source.

In some embodiments the sensing step comprises sensing electrical energy at a sensing region that is outside of a stimulation region demarcated by boundaries of a plurality of stimulation electrodes placed proximate to the muscle being stimulated.

In some embodiments the sensing step comprises sensing electrical activity indicative of a state of a tendon coupled to the muscle.

In some embodiments the sensing step comprises sensing electrical activity that is indicative of a bulkening muscle.

In some embodiments the sensing step comprises sensing electrical activity that is indicative of a proximity to a dynamic structure.

In some embodiments the sensing step comprises sensing a change in the electrical energy that occurs between the stimulation region and the sensing region.

In some embodiments the sensing step comprises sensing a first electrical stimulating signal with a first parameter delivered to the muscle from the external electrical energy source, the method further comprises: sensing a second electrical stimulating signal delivered to the muscle from the external electrical energy source, wherein the second electrical stimulating signal has a second parameter different than the first parameter; and comparing the sensed first electrical stimulating signal with the sensed second electrical stimulating signal and determining whether the first electrical stimulating signal or the second electrical stimulating signal results in a more efficient muscle contraction, wherein the applying step comprises applying the first or the second electrical stimulating signal depending on which signal results in a more efficient muscle contraction. Determining whether the first electrical stimulating signal or the second electrical stimulating signal results in a more efficient muscle contraction comprises analyzing how the peak voltage amplitude of individual pulses contained within the first and second signals change over time. During analysis some data processing steps may be implemented, for example steps to account for different amplitudes of the applied first and second electrical stimulating signals. The first parameter can be a first energy intensity and the second parameter can be a second energy intensity different than the first energy intensity.

One aspect of the disclosure is a muscle stimulation system, including at least one stimulating electrode adapted to apply a stimulating electrical signal to a muscle at a stimulation region; at least one sensor adapted to sense the stimulating electrical signal or a change in the stimulating electrical signal at a sensing region; and a control unit adapted to analyze the sensed stimulating electrical signal or a change in the stimulating electrical signal that occurs between the stimulation region and the sensing region.

In some embodiments the control unit is adapted to modify at least one parameter of the stimulating electrical signal, deliver a second stimulating electrical signal to the at least one stimulating electrode with the modified parameter, and compare a second sensed stimulating electrical signal with the sensed stimulating electrical signal.

In some embodiments the control unit is further adapted to determine which of the second stimulating electrical signal and the stimulating electrical signal results in a more efficient muscle contraction. The control unit can be adapted to automatically deliver a muscle stimulation therapy to the muscle with either the second stimulating electrical signal or the stimulating electrical signal depending on which results in a more efficient muscle contraction.

In some embodiments the control unit is adapted to analyze the peak voltage amplitude of the sensed stimulating electrical signal.

One aspect of the disclosure is a method of electrically stimulating muscle comprising: delivering a first electrical muscle stimulation signal to a muscle region of the patient; sensing a signal indicative of a state of a tendon coupled to the muscle during the delivering step; and delivering a second electrical muscle stimulation signal to the muscle region with at least one signal parameter modified based on the sensed signal indicative of the state of the tendon.

In some embodiments the sensing step comprises sensing a signal indicative of a change in the state of a tendon coupled to the muscle.

In some embodiments the sensing step comprises sensing a signal indicative of a state of tension in the tendon coupled to the muscle.

In some embodiments the sensing step comprises performing an ultrasound analysis of the tendon when delivering the first electrical muscle stimulation signal.

In some embodiments the sensing step comprises sensing, at a sensing region on the body, an electrical signal that is applied to the body by an external source at a stimulation region on the body. The signal applied by the external source is applied when the muscle stimulation energy is applied to the stimulation region.

One aspect of the disclosure is a system for electrical muscle stimulation, comprising: a first sensing pad comprising at least one electrical sensor and an anatomical marker adapted to align with a readily identifiable anatomical feature, wherein the anatomical marker allows the stimulation pad to be positioned on a patient's body in a particular location; and a stimulation pad comprising at least one electrical stimulation electrode, wherein the first sensing pad further comprises a first alignment marker that corresponds with a second alignment marker on the stimulation pad, wherein the corresponding first and second alignment markers allow a desired positioning of the stimulation pad on the user's body by aligning the first and second markers.

In some embodiments the anatomical marker is an aperture, such as one sized and configured to accommodate the patient's knee.

In some embodiments the first alignment marker has a first shape and the second alignment marker has a second shape, wherein the first and second shapes are complementary.

BRIEF DESCRIPTION OF THE DRAWINGS

FIGS. 3A-B illustrate an exemplar of sensed signals that originate in an external electrical energy source.

FIG. 5A-E illustrate exemplary arrangements of a stimulation pad.

FIG. 5F illustrates a stimulation pad comprising electrodes from a top-view on a body part of a user. FIG. 5G illustrates a stimulation pad containing electrodes from a side or profile view on the body part of a user. In preferable embodiments, the stimulation pad may be thin, soft, and flexible.

FIG. 6A illustrates an exemplary muscle stimulation system.

FIG. 6B(i)-(ii) show a top and side views of one embodiment of a sensor pad.

FIGS. 6C-F illustrate implementations of a sensor pad.

FIG. 6 G illustrates an exemplary embodiment of a muscle stimulation system.

FIGS. 7A(i)-(ii)-C illustrate an exemplary embodiment of a muscle stimulation system and exemplary method of use.

FIGS. 8A-8D illustrate several example implementations of stimulation and sensor pads that have coordinating or complementary geometries.

DETAILED DESCRIPTION

Figure 1:
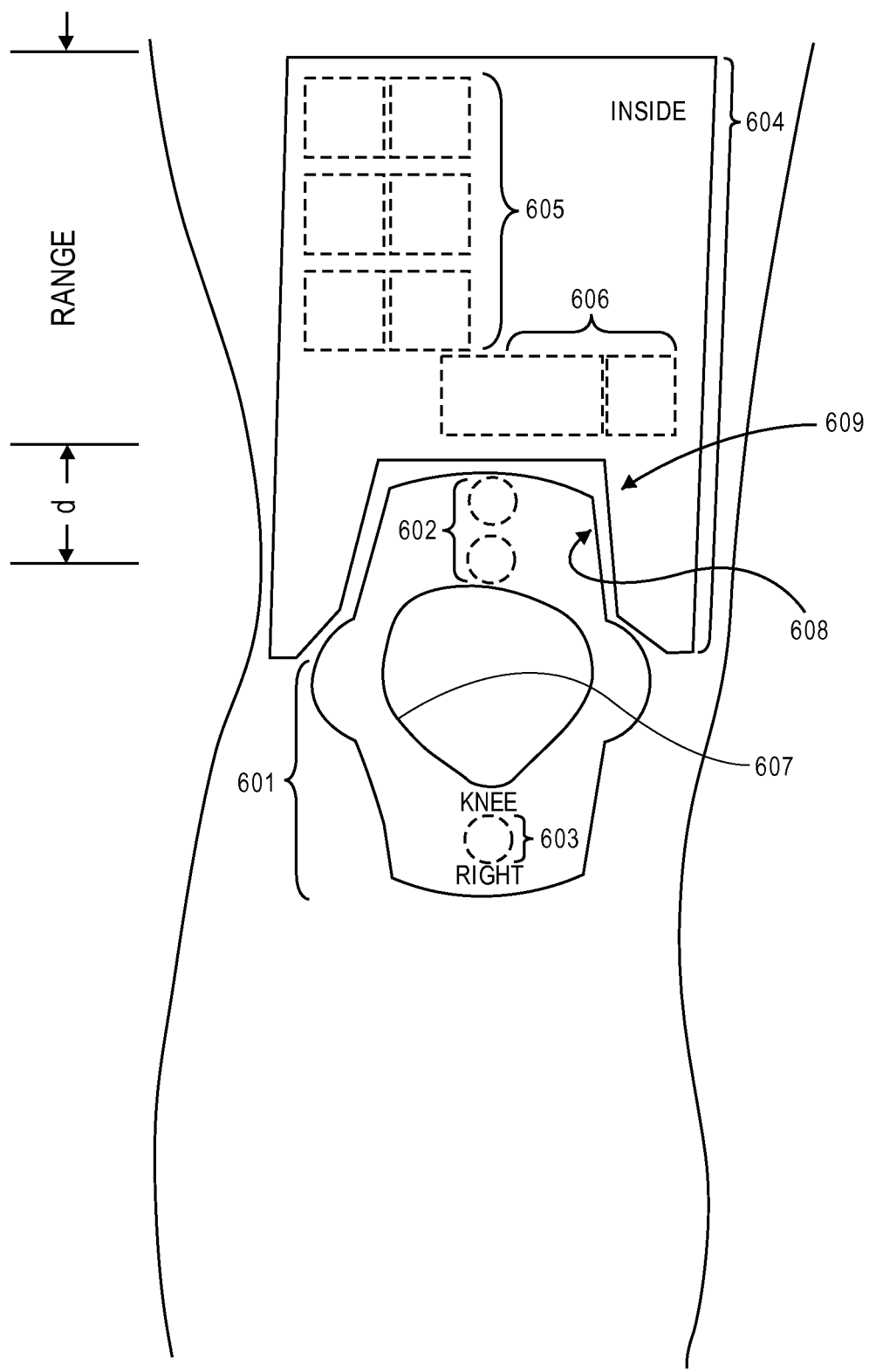
FIG. 1 illustrates a portion of an exemplary muscle stimulation system.

This disclosure generally describes devices, systems, and methods for automated optimization of energy delivery to human or animal tissue. Though this disclosure uses the modality of NMES as an illustrative example, with minor modifications the devices, systems, and methods described herein may be applied with utility to other energy-delivery therapies, such as TENS or RF or microwave ablative therapies. One objective of the presently-disclosed devices, systems, and methods is to simultaneously increase the effectiveness of energy delivery by selecting optimum parameters and/or energy delivery locations for use and to decrease the operator-time required in order to deliver a safe and effective therapy, such as NMES therapy. In preferable embodiments of the presently-disclosed devices, systems, and methods, this multi-faceted improvement to NMES state-of-the-art is achieved through the use of an inventive sensor system that is functionally superior to NMES sensor systems described previously. Some exemplary embodiments involve the use of tendon-based sensors that examine anatomical properties indicative of the degree of muscle contraction. Some implementations will include newly-developed signal processing steps that examine signal characteristics and sensor data patterns that have not been recognized in previous attempts.

In some preferable embodiments of the devices, systems, and methods herein, at least one sensor (such as a sensor similar to an EKG sensor) capable of extracting electrical signals from the surface of the body is placed on a sensing region of the body that is different than and away from the stimulation region. A large portion of the electrical signals sensed by the one or more sensors is the electrical energy delivered to the body by external sources, such as a control unit. The at least one sensor senses how the contracting muscle alters the applied energy as it travels from the stimulation region to the sensing region. Sensing a signal that originates from an external electrical source is different than the sensing that occurs in, for example, EKG or EMG data collection. In EKG or EMG, the sensors sense signals that arise originally from within the body due to cardiac or skeletal muscle contraction and accompanying bioelectricity. While the sensors herein may structurally be similar to those used for EKG or EMG data collection, the devices, systems, and methods herein are vastly different from those well-established clinical measurement techniques. Additionally, the devices, systems and methods herein are further differentiated from the aforementioned techniques because of, for example without limitation, detection techniques, sampling and filtering methods, and signal processing algorithms and other decision-making software associated with the devices, systems, and methods herein.

One aspect of the disclosure is a method of electrically stimulating a muscle, wherein the method includes sensing electrical energy delivered to a muscle from an external electrical energy source, and applying an electrical muscle stimulating signal to the muscle to stimulate the muscle, wherein at least one parameter of the electrical muscle stimulating signal is based on the sensed electrical energy delivered from the external energy source.

The benefits to this aspect over previously described sensors such as EMG, accelerometer, strain gauge, etc., are numerous. For example, this aspect overcomes the EMG signal-to-noise ratio issues described above by capturing and processing a strong electrical signal in a region with little to no unwanted electrical noise.

Various aspects of the systems and devices described herein can be applied to any of the particular applications set forth below or for any other types of electrical stimulation and sensing systems or methods. Parts of the devices and systems can be applied as a standalone system or method, or as part of an integrated medical treatment system. It shall be understood that different aspects of the disclosure can be appreciated individually, collectively, or in combination with each other.

An exemplary system adapted to perform the aspect above includes three core components: surface stimulation electrodes used to couple electrical energy into and out of the body at a stimulation region, at least one sensor adapted to sense a change in the delivered electrical energy that occurs between the stimulation region and the sensing region; and a control unit adapted to generate the electrical muscle stimulation signal and deliver it to the at least one surface stimulation electrode, and to analyze the sensed signal from the at least one sensor. The sensor is positioned on the body at a location other than where the energy is delivered to the surface of the body. In some embodiments this involves positioning a sensing electrode at a location on a patient's body other than where a stimulation electrode is positioned on the body. The control unit is adapted to communicate with the surface stimulation electrodes and the at least one sensor in a manner suitable for transmitting and receiving electrical signals, such as with a standard cable connection, a wireless connection such as Blue-tooth, WiFi, infrared, or other similar connections.

In some embodiments the method assesses a sensed signal that is indicative of a state of one or more tendons coupled to the stimulated muscle. Without wishing to be bound by any theory, it is believed that the geometry, mechanical properties, and/or other characteristics of the tendon influence its electrical properties. Suganuma et al., J Ortho Science 9: 302-309, 2004 ("Suganuma"), incorporated herein by reference, generally describes how characteristics of a tendon can influence transmission speed and impedance. Thus, changes in the state of the tendon may affect electrical signals transmitted to the sensing electrodes from the stimulation region. Tendons connect muscles to bones, and transmit forces that arise due to muscle contraction. Accordingly, tendons are capable of withstanding tension during muscle contraction. Without wishing to be bound by any theory, it is believed that a stronger muscle contraction produces more tension and a greater geometry change in an associated tendon and adjacent anatomical regions than a weaker muscle contraction. It would follow that a stronger muscle contraction would alter both the electrical properties of the tendon and the available electrical transmission pathways, and thus the electrical activity detected by the sensing electrodes located over or beyond the tendon, more than a weaker muscle contraction. Specifically, it is believed (as proposed by Suganuma) that increased tendon tension leads to increases in tendon electrical impedance. Thus, electrical activity detected over or near tendons is suitable for optimization of techniques, including electrical stimulation, that produce muscle contraction and induce changes in tendon geometry and tension.

Sensing signals from electrodes placed over tendons and inventive signal processing algorithms developed to assess the effects of tendon properties and geometry on recorded signals offer many advantages over traditional NMES optimization methods. Standard electromyography (EMG), defined here as measuring the electrical activity produced by muscle contraction using surface or needle electrodes placed in the region of contracting muscles, has limited usefulness during electrical stimulation due to interference between electrical signals injected into the body by the stimulator (on the order of 10-50 V) and electrical signals produced by muscles (on the order of 5-50 mV). Current clinical and engineering research has focused upon the development of complex, often adaptive, signal filters to extract useful information from EMG data collected during electrical stimulation. However, problems with extracting useful EMG data during electrical stimulation are exacerbated when an array of stimulation electrodes are used, because the interference pattern between the stimulation energy artifact and the muscle activity data will not be constant among all data acquisitions, leaving previously developed EMG filters generally not applicable or of limited utility. As described in detail below, signal processing algorithms that extract information indicative of a state of a tendon from electrical signals recorded over tendons do not suffer from performance degradations or interpretation uncertainty due to electrical stimulation/EMG signal interference.

When muscle stimulation is applied to critically ill patients, further advantages of optimization methods based upon tendon tension and/or geometry are evident. In the ICU and many other environments, the use of needle electrodes to measure EMG data is generally not suitable, and surface electrodes must be used. Critically ill patients often suffer from tissue edema (swelling) as a side effect of treatment. It is believed that the presence of significant edema will generally result in a greater distance between muscle tissues and the skin, attenuating and distorting EMG data that are collected with electrodes on the skin surface. In many cases, no useful EMG data can be acquired. Similar problems exist when using surface electrodes to measure EMG data from obese persons or persons with low baseline muscle mass. Deposits of fatty tissue and tissue edema are typically at local minima around bony prominences, such as the knee, where tendons insert. Thus, electrical activity measured over the tendon (or, as shown below, even over the bony prominence itself) may produce data more reliable than EMG data in these persons. Signal processing algorithms developed to interpret these data may thus enable indirect measurement of muscle contraction when useful EMG data are unobtainable. Additionally, critically ill patients are most often treated while lying in bed with legs extended. As legs are already extended, the stimulation of the quadriceps produces little physical movement, limiting the utility of sensors such as accelerometers that seek to optimize the electrical stimulation location or parameters based upon measurements of muscle dynamics.

FIG. 1 illustrates a portion of an exemplary system that can be used to sense signals indicative of a state of a tendon and use them to adjust at least one parameter of an electrical muscle stimulation signal and/or optimize the location of stimulation to contract a muscle. The system includes sensing pad 601 and stimulating pad 604. Sensing pad 601 includes sensing electrodes 602 and reference electrode 603. Stimulating pad 604 includes a plurality of electrodes, or an array of electrodes, including a first group of electrodes 605 and a second group of electrodes 606. Sensing pad 601 includes an anatomical marker 607 that is adapted to align with a readily identifiable anatomical feature, wherein the anatomical marker allows the stimulation pad to be positioned on a patient's body in a particular location. Sensing pad 601 also includes first alignment marker 608 that corresponds with a second alignment marker 609 on stimulation pad 604, wherein the corresponding first and second alignment markers allow a desired positioning of stimulation pad 604 on the user's body by aligning the first and second markers. In variations on the embodiment in FIG. 1, a plurality of stimulating electrodes and a plurality of sensing electrodes are assembled into a unitary pad structure or other pre-assembled configuration.

FIG. 1 illustrates stimulation electrodes that are positioned on a leg of a patient to stimulate a quadricep muscle. The sensing electrodes 602 are disposed on the leg in a position superior to the knee in the region of the quadriceps tendon, and are away from the location of the stimulating electrodes.

Stimulation pad 604 includes an array of stimulation electrodes, each of which can be individually enabled or disabled automatically by a control unit to provide electrical energy to the muscle. Using an array of electrodes that can be individually enabled and disabled enables the gross placement of stimulation pad 604 on a person in a desired region of stimulation without requiring precise alignment of individual electrodes over the motor points of the muscle. The stimulation pad can include any suitable number of electrodes, such as one, two, three, four, six, nine, ten, twelve, fifteen, twenty, or more. The stimulation electrodes can be disposed at any location on the stimulation pad.

In some embodiments the stimulation pad comprises an array of eight square or rectangular stimulation electrode contacts arranged in a particular pattern. Other arrangements of the stimulation electrode array, and other electrode contact shapes and sizes, can also be used. Stimulation pads configured to be used with muscle groups other than the quadriceps can be configured with stimulation electrode arrays that have different electrode arrangements than the array shown in the exemplary embodiment in FIG. 1.

In this exemplary embodiment sensing pad 601 includes three sensing electrodes. Sensing electrodes 602 are adapted to sense electrical stimulation signals that original in the control unit and are delivered to the muscle via the stimulating electrodes. The sensed signals are communicated back to the control unit for analysis, as set forth below. Sensing pad 601 also includes reference electrode 603, or ground electrode, that is positioned over a bony prominence some distance from sensing electrodes 602. For example, reference electrode 603 can be positioned over the shin near the tibia. Alternatively, as few as one sensing electrode can be used to extract sufficient information required to optimize electrical stimulation parameters. Similarly, at least one sensing electrode and at least one ground electrode may be provided.

In some embodiments more than three sensing electrodes extract information concerning the state of the tendon, such as tendon tension and/or tendon geometry. In these embodiments, information from individual sensing electrodes may be analyzed individually, and may or may not be compared with the use of a differential amplifier or similar hardware or software.

Sensing electrodes 602 are positioned on the body at the lower thigh above the knee cap. In some instances, they are vertically directly above the knee cap, while in other embodiments, they are horizontally spaced. They can be in other positions with respect to the knee.

The sensing electrodes are arranged some distance from the reference electrode. In some embodiments the reference electrode receives very little or no electrical signals that are provided from the stimulation electrodes. A reference electrode may pick up inherent background electrical signals from the subject body. In some instances, the signals collected by the sensing electrodes are compared to the signals sensed by the reference electrode to determine which signals are provided by the stimulation electrodes and muscle properties, and which are provided by background signals. In some instances, the background signals provided by the reference electrode may be subtracted from the signals collected by the sensing electrodes.

Sensing pad 601 includes an anatomical marker 607 in the form of an aperture adapted to align with a readily identifiable anatomical feature, in this embodiment a knee cap. In this embodiment the apertures accommodates the knee cap protrusion. The anatomical marker allows the sensing pad to be positioned on a patient's body in a particular location and orientation, and in this embodiment to ensure proper placement of the sensing electrodes over a particular location, in this embodiment the quadriceps tendon. In some embodiments the anatomical marker is a different material over the knee cap region that enables the knee cap to more easily stretch the sensing pad at the knee cap. The marker can also be a visual indicator, such as a color change or line that may indicate the placement of the knee cap. Thus, the sensing pad may include an anatomical placement marker that assists with positioning the sensors at a desired location and/or orientation relative to an anatomical feature of the body.

Sensing pad 601 also includes first alignment marker 608 that corresponds with a second alignment marker 609 on stimulation pad 604, wherein the corresponding first and second alignment markers allow a desired positioning of stimulation pad 604 on the user's body by aligning the first and second alignment markers. Once sensing pad 601 is positioned at a given position, stimulation pad 604 can be positioned relative to sensing pad 601 by aligning the two alignment markers. The alignment markers are adapted to allow the stimulation electrodes to be positioned on the body in certain locations by aligning the two alignment markers.

In this embodiment the first and second alignment markers are complimentary shapes. In particular, the top portion of the sensing pad forms a protrusion with a shape that is complimentary to a notch-shaped alignment marker in stimulation pad 604. Any shapes that allow the sensing pad to align with the stimulation pad can be used.

This geometry may allow for the usefulness of the knee cap as an anatomical marker to be extended to aid in accurate gross positioning of the stimulation electrode array. This geometry may increase both intra- and inter-operator consistency of stimulation pad placement by creating a virtual anatomical reference point (the anatomical marker of the sensing pad) in a region of the body (e.g., the thigh) that lacks readily identifiable anatomical features. Additionally, this geometry may be designed specifically to fix the position of the stimulation electrodes with regard to the sensing electrodes, and to minimize deviations from the ideal spatial relationship between the two sets of electrodes. In some embodiments, additional visual indicators or markers, such as arrows on the sensing and stimulation pads, may provide additional aids in aligning the sensing and stimulation pads. Thus, visual markers may aid in fixing the spatial relationship of the sensing and stimulation pads.

The exemplary system shown in FIG. 1 can be used to automatically optimize NMES parameters and/or locations. The array of stimulation electrodes includes first group 605 in which the electrodes are located near the bulky part of the thigh, and second group 606 in which electrodes are located more inferior than first group 605 closer to the quadriceps tendon. In some embodiments of NMES therapy the energy delivered by the control unit travel between one or more upper electrodes 605 and one or more lower electrodes 606. Upper electrodes may be positioned to make contact with the middle-outside of a person's thigh (expected location of a motor point), and span a length (for example, six inches) expected to be larger than the span of possible motor point locations in an average adult. Lower electrodes may also be positioned close to the location of an expected muscle motor point, and can also be positioned in a manner so as to dictate the direction of current flow through the leg. In some embodiments, an exemplary larger lower electrode shown need not be centered along the midline of the thigh. Instead, it may be arranged so that its center point is slightly toward the inside of the thigh, causing energy traveling between the upper and lower electrodes to cross the midline of the thigh. An additional, smaller lower electrode, is shown positioned at a similar distance superior to the knee cap as the wider lower electrode, but disposed closer to the inside of the leg. The placement of the electrodes, or the placement of the pad, can also depend on the target muscular stimulation.

In this embodiment the system also includes one or more sensing electrodes 602 adapted to sense a signal originated from an external energy source. In particular, the sensors 602 are adapted to sense how the stimulating energy delivered from the control unit changes between the stimulation location on the body and the sensing region on the body. The sensors 602 are thus adapted to sense how the contracting muscle, and perhaps other parts of the anatomy, change the stimulation energy that is applied from the external energy source between the stimulation region on the body and the sensing region on the body.

The system also includes a control unit connected to at least one stimulation electrode and to at least one sensing electrode. The control unit provides stimulation signals to the stimulation electrodes and receives signals from the sensing electrodes. The control unit is also generally adapted to modify at least one parameter of a stimulation signal based on the sensed signals from the sensors to automatically optimize the stimulation energy applied to the muscle.

The control can be integrated into a sensing pad, a stimulation pad, or an integral pad when stimulation and sensing pads are integral. The control unit can be considered a separate structure not rigidly coupled to either the stimulation pad or the sensing pad, such as a separate structural component in wired or wireless connection with the stimulating and sensing electrodes. The control unit can be adapted to be positioned on a bedside table next to a patient. In some embodiments the control unit is a micro controller rigidly fixed to the stimulation or sensing pads. Additional exemplary details of a control unit can be found in U.S. Pub. No. 2010/0004715, filed Jul. 2, 2009, now U.S. Pat. No. 8,285,381, which is fully incorporated by reference herein.

Figure 2:
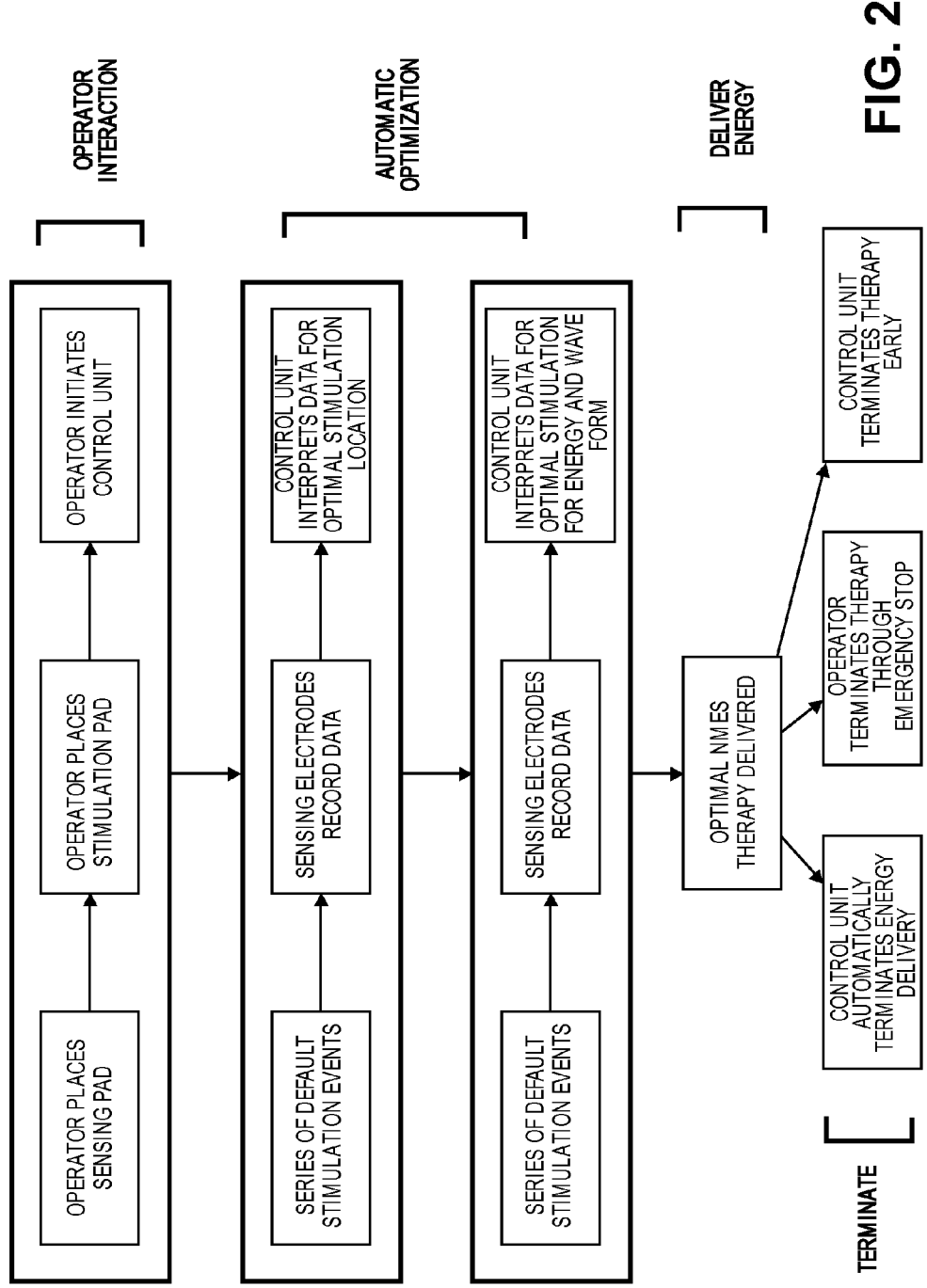
FIG. 2 illustrates an exemplary method of automatically optimizing muscle stimulation parameters.

FIG. 2 is a flow chart outlining exemplary steps in an exemplary method of optimizing muscle stimulation energy. In this embodiment the general steps include, as shown, operator interaction, automatic optimization, energy delivery, and termination. Any of the steps described may be optional, interchangeable with another step, or may occur in a different order than described. For example, operator interaction can include (1) an operator placing a sensing pad on a subject, (2) an operator placing a stimulation pad on a subject, and (3) an operator initiating or activating a control unit.

The general automatic optimization step, which can also be referred to herein as a calibration procedure, can include steps that the control unit automatically performs to determine optimal stimulation energy parameters and/or stimulation locations for subsequent NMES therapy. The general automatic optimization step is shown including two general functions: 1) determining optimal location for stimulation; and 2) determining optimal energy and waveform for the NMES stimulation signal. The automatic optimization can include (1) running a series of default stimulation events, (2) using sensing electrodes to sense data from the default stimulation events, and (3) a control unit interpreting the sensing electrode data to determine an optimal stimulation location, which can include determining optimal electrodes to be used in subsequent NMES therapy. Automatic optimization can also include (4) providing a series of default stimulation events, (5) having sensing electrodes sense data from the stimulation events, and (6) interpreting data to determine optimal stimulation energy and waveform. These steps may occur repeatedly, periodically, and/or continuously throughout the NMES method.

The energy delivery step includes delivering an optimal NMES therapy based on the results from the data processing during the automatic optimization step(s). The signal to be provided by the stimulation electrodes during NMES therapy may be determined by one or more algorithms in a control unit during the automatic optimization.

The termination step occurs when the control unit automatically terminates energy delivery, when an operator terminates therapy through an emergency or otherwise user-initiated stop, or when the control unit terminates therapy early. These exemplary steps are discussed throughout the disclosure in more detail.

An operator can begin the method by placing sensing and stimulating pads on the person receiving therapy. For example, the operator can use a system with pads such as those shown in FIG. 1 and can use the anatomical markers and/or alignment markers such that the sensing and stimulation pads will be positioned in proper places without extensive operator placement training. Once the pads are in place, the operator may initiate therapy by activating an actuator, such as pressing a button, flipping a switch, connecting two components, or another suitable action. Following this action, no additional operator actions may be required to determine optimized stimulation parameters and/or locations and deliver NMES to the patient. After the control unit is initiated, an algorithm programmed with the series of default stimulation events can control the delivery of sequential stimulation energy waveforms of known shape, duration, and amplitude to pairs or groups of stimulation electrodes in the array of electrodes. Although a great number of stimulation waveforms can be used for these default stimulation events, a merely exemplary waveform is characterized by a 5 second train of asymmetric, biphasic square wave pulses of 300 µs duration and 50 mA average peak electrical current repeating at a rate of 40 Hz, with the train having amplitude ramp-up and ramp-down periods of 1 second (i.e., 3 seconds of full amplitude energy delivery).

During each stimulation event, sensing electrodes simultaneously sense the electrical activity over the tendon. The sensors sense the electrical energy delivered from the control unit as it changes between the stimulation region on the body to where it is sensed in the sensing region. For example, is this embodiment the sensors sense how the contracting muscles and tendons alter the externally delivered energy signal as it travels from the stimulation region to the sensing region. This sensed electrical activity may represent some combination of the stimulation energy directed into the body by the control unit and the underlying muscle electrical activity (i.e., M-waves) resulting from contraction. Sensed data is transmitted to the control unit where it is received as input as part of the automatic optimization, and can be stored in a memory location as either raw or processed data. In some embodiments the electronics for processing the sensed signals are incorporated onto a sensing pad rather than being part of a separate external device. That is, the control unit can be considered part of the sensing and/or stimulation pads. Processing the sensed signals can include filtering steps such as high or low pass filters, as well as adaptive and/or non-linear signal processing to remove electrical activity produced by the stimulation electrodes and other electrical noise generated by the surrounding environment.

Following the execution of a plurality of default stimulation events and the storing of the electrical activity sensed during each event in memory, algorithms located in the control unit or on either the sensing or stimulation pad compare the various electrical activity waveforms sensed by the sensing electrodes. For example, sensed signals from a sub-threshold or low amplitude stimulation may be compared to sensed signals from a super-threshold or high level stimulation. In this embodiment the comparison searches for the pair or group of stimulation electrodes in the stimulation array that produced the strongest and/or most efficient muscle contraction. In this manner the algorithm can automatically determine the most optimal stimulation electrode location, or it can determine which electrodes in the array should be used in the NMES therapy to most effectively stimulate the muscle.

The control unit has electronics such as a microprocessor, FPGA, or other suitable means that allow it to execute algorithms that process the sensed data. For example, the control unit can include algorithms that measure the total energy in the sensed electrical waveforms, the relative energy drop detected between pairs of sensing electrodes, the energy located in certain portions of the electrical waveforms, or the slope of waveform energy change vs. the amplitude of energy delivered to the body by the stimulation electrodes.

Experience has shown that the shape or type of the electrical activity waveforms sensed over the quadriceps tendon varies based upon the placement of the active (i.e., used to deliver and/or receive energy) electrode(s) relative to the tendon. It is believed that the shape or type of the sensed electrical activity waveform is a function of the muscles stimulated by a given pair or group of electrodes, the state of the tendon induced by the muscle contraction, the electrical path between stimulation electrodes, sensing electrodes, and other local anatomy, and potentially other factors. It is thus believed that similar phenomena may alter the shape of electrical activity waveforms sensed around tendons in other anatomical regions, as well. Knowledge of the shape or type of the waveform may in some instances be vital for successful implementation of the disclosed methods. Specifically, it may be important and preferable that each potentially used pair or group of stimulation electrodes produces the same general shape or general type of electrical activity waveform, as measured by sensing electrodes placed on or nearby the tendon. While waveforms of the same general shape or type can be compared accurately with signal processing algorithms to search for subtle differences resulting from differing electrical properties of the tendon, comparison of waveforms with markedly dissimilar shapes will generally miss these subtle differences.

FIGS. 3A and 3B illustrate example electrical activity waveforms sensed by sensing electrodes placed over a quadriceps tendon. Although each waveform may be a single electrical trace, sensed portions of interest (what may be defined as the response pulses) in the waveforms have been highlighted for illustrative purposes. The electrical activity waveforms may include examples of the large stimulation pulses 901, examples of monophasic response pulses 902, and examples of biphasic response pulses 903. In embodiments in which the stimulation assembly includes lower electrodes, the lower electrodes may be positioned to produce the electrical activity waveforms. A major factor in the determination of waveform shape may be the location of lower stimulation electrode(s) with respect to the quadriceps tendon.

FIGS. 3A and 3B show examples of two different sensed electrical activity waveform shapes resulting from stimulation of the quadriceps muscle. Waveforms were recorded with sensing electrodes arranged and placed as shown in the embodiment in FIG. 1 and with the two superior located sensing electrodes 602 sensing data that was the input data to a differential amplifier circuit. These examples are provided for illustrative purposes, and those skilled in the art will recognize that other waveform shapes are probable in different anatomical locations and that different stimulation electrode array configurations and sensing electrode locations will produce variations of the depicted waveform shapes as detected over the quadriceps tendon. Depicted in FIG. 3A is a subset (zoom-in) of the electrical activity sensed when the smaller lower stimulating electrode was disabled and the center of the larger lower stimulating electrode was located slightly to the outer side of the quadriceps tendon. Depicted in FIG. 3B is a subset (zoom-in) of the electrical activity sensed by sensing electrodes when the smaller lower electrode is disabled and the center of the larger lower electrode may be located slightly to the inner side of the quadriceps tendon.

Both of the electrical activity waveform shapes shown in FIGS. 3A and 3B are comprised of two sets of pulses that repeat at the rate of stimulation (in this exemplary embodiment, 40 Hz). The larger amplitude pulses 901 may be related to stimulation electrical energy supplied by the control unit via the stimulation electrodes. The smaller pulses, 902 and 903, may result from the electrical activity produced by muscle contraction (i.e. EMG M-waves), any residual effects of the stimulation energy supplied by the control unit, and potentially other sources. These smaller pulses may also be referred to herein as response pulses. The shape of these response pulses is generally important to enable effective comparison. In this disclosure, the shape of the response indicated by 902 may be monophasic and the shape of the response indicated by 903 may be biphasic.

In some embodiments it is desirable to use sensed electrical activity waveforms with biphasic response pulse shapes. The biphasic waveform response may optimize the tradeoff between the predictive power (with regard to ideal muscle stimulation location and strength) of the electrical activity detected by the sensing electrodes and the quality of the muscle contraction induced in the quadriceps muscle. Without wishing to be bound by any theory, it is further believed that biphasic nature of the response pulse arises when conditions allow for a portion of the original electrical activity waveform to interfere with other electrical activity measured by the sensing electrodes. This interfering electrical activity could originate from M-wave or stimulus pulse reflections from the tendon or surrounding anatomy, H-reflex interference, or from other sources.

When using the exemplary stimulation pad and sensing pad geometries shown in FIG. 1, most NMES operators will place the stimulation pad in a way such that the muscle stimulation induced by sending energy between any upper electrode in the array and only the larger lower electrode will produce an electrical activity waveform detected by the sensing electrodes that has a biphasic shape. In some embodiments, depending on the placement of the stimulation electrodes, software algorithms can be used to verify proper placement of the stimulation pad by ensuring that the electrical activity waveform recorded by sensing electrodes contains biphasic response pulses. For example, this could be done by comparing the maximum positive and negative amplitudes of the response pulses (not of the larger stimulation pulses indicated by 901). If the response pulses were determined to not be suitably biphasic, the smaller lower stimulation electrode may be activated such that stimulation energy travels between one or more upper stimulation electrodes and both lower stimulation electrodes in tandem. This effectively shifts the lower stimulation energy location more to the inside of the leg, making the response pulses detected by the sensing electrodes more biphasic, and thus more useful. The systems can thus be used to determine what combination of stimulating electrodes will produce an effective response signal.

In this embodiment, following the initial series of preset stimulation events, the storage of electrical activity waveforms in memory, and confirmation that the electrical activity waveforms produced by each pair or group of stimulation electrodes all contain generally the same shaped response pulses (e.g., biphasic, monophasic, or another shape not explicitly illustrated in this disclosure), signal processing algorithms compare the electrical activity waveforms to determine which pair or group of stimulation electrodes may be most optimized for use (e.g., closest to muscle motor points) during NMES therapy. In this aspect these comparisons can be performed by assessing the sensed electrical waveforms for indications of state of the tendon, such as tendon tension. Stronger muscle contraction may lead to more tendon tension, leading to both increases in the electrical impedance of the tendon and geometry changes in the tendon and surrounding anatomy. It is believed that these tendon changes may further lead to an increased amplitude of electrical activity being measured at the tendon. This increase in energy may be due to increased reflection of energy at or near the tendon. Similar to physics governing transmission line theory, as electrical waveforms encounter resistive loads, a portion of the waveform is absorbed by the load (in this case, tendon) and a portion is reflected. Waveform reflections may also arise due to changes in geometry of the tendon or surrounding anatomical structures that may change geometry in response to increased tension in the tendon. It is also possible that energy increases may arise from other sources, such as H-reflex interference or other factors. Signal processing mechanisms may be utilized to extract the energy contained in response pulses as an indirect but accurate measure of muscle contraction strength. This method may offer significant advantages over EMG and other measures of muscle contraction strength in critically ill and other groups of persons, and can thus enable more accurate and reliable optimization of NMES.

Thus, in some embodiments, a sensor located over or near a tendon may measure large amplitude pulses (e.g., comparable to 901) from a stimulation electrode. In some embodiments, a tendon sensor may measure relatively little or no EMG signals. In some instances, no further amplification of the signal received from the sensor may be necessary. Thus, preferably, the signal received by a tendon sensor (located over or near a tendon) may be unamplified. For instance, no differential amplifier may be used to increase smaller pulses (e.g., pulses comparable to 902 and 903). As an illustrative example, FIG. 9 shows sensed signals captured in one embodiment of a sensor system that does not use amplification other than using the sensed signal at a second electrode as a ground reference point. In alternate embodiments, some amplification may occur. Thus, as previously mentioned, the use of a tendon sensor may offer an advantage over traditional EMG by not requiring additional amplification components.

In the exemplary embodiment of the system shown in FIG. 1, sensing electrodes 602 may be configured to each serve as an input to a two-channel differential amplifier. In this configuration, the sensing electrodes may be used to collect data that are indicative of reflection and other tendon-induced changes in the response pulse shape, amplitude, and other characteristics. In this configuration, the stimulation electrode pair or group that produces the strongest muscle contraction may produce response pulses that contain the most energy. The major differentiator in the energy contained in the response pulses may be related to the amount of tension in the tendon. In some embodiments, signal processing methods may extract the total energy contained in the response pulses by: i) filtering out or removing larger stimulation pulses (e.g., those of type indicated by 901) from the recorded electrical activity waveform, ii) taking the absolute value or the envelope of the remaining waveform, iii) integrating or tallying a cumulative sum of remaining waveform data to estimate the total energy of the response pulses contained in the waveform. Step iii) allows for small amplitude differences that occur repeatedly over many stimulation events to produce more robust (i.e., higher contrast) energy estimates. Alternative signal processing methods could only apply to steps ii)

and iii) without filtering out or removing the larger stimulation pulses from the recorded electrical activity waveform. An alternative embodiment of the method involves a more extensive series of preset stimulation events, with the default stimulation train applied to each potential pair or group of stimulation electrodes being repeated with two or more average electrical current amplitude levels. In this scenario, signal processing algorithms could implement steps i)—iii) as outlined above, but may also add a fourth step that determines how the energy contained in the electrical activity waveform changes with changes in the applied stimulation energy. Without wishing to be bound by any theory, it is believed that the pair or group of stimulation electrodes that produces the largest change in sensed electrical activity energy with increasing applied stimulation energy will be the most suitable for providing effective NMES therapy. In further embodiments of the method, analysis could involve the use of amplitude threshold detectors, integrator circuits or algorithms, comparator circuits or algorithms, or other similar techniques.

Given the belief that changes in tendon tension and/or geometry may cause changes in the degree of reflection (if any) of the response pulses or other changes (e.g., from H-reflex or other sources) in the interference pattern measured by the sensing electrodes, a variation of an embodiment of the system and signal processing described above is possible.

Figure 4A:
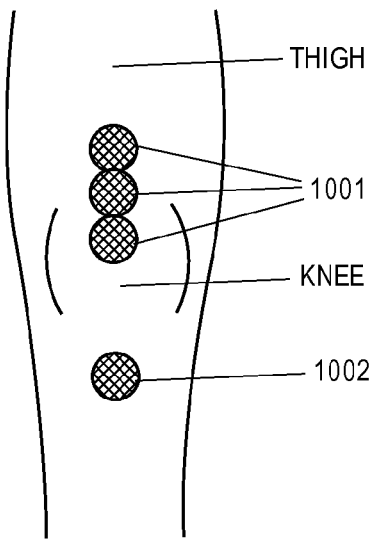
FIGS. 4A-C illustrate exemplary sensing electrode positioning and a comparison of sensed signals.

An alternative exemplary position of sensing electrodes is shown in FIG. 4A. In this configuration, three sensing electrodes 1001 near the knee, referred to individually as the superior, middle, and inferior electrodes, may be utilized to sense electrical signals for analysis. A fourth sensing electrode 1002 that acts as a reference may be located over a bony prominence further from the region of stimulation, for example over the shin. Each non-ground sensing electrode may collect waveform voltage data (with reference to the reference electrode) individually. In some configurations, the voltage signals from the superior or middle electrodes may be used as one input to a differential amplifier, with the signal from the inferior electrode serving as the second input to the differential amplifier, with the ground electrode signal serving as circuit ground. In some other configurations, no differential amplifier is used in conjunction with the superior, middle, and inferior electrodes. As previously discussed, any arrangement or number of sensing electrodes may be utilized.

In one implementation, the superior and middle electrodes may be placed at the lower thigh directly superior to the knee. The inferior electrode may be placed directly on the knee cap. In some instances, the tendon may be stretched over the knee cap and the inferior sensing electrode on the knee cap may be in electrical communication with the underlying tendon. The reference electrode may be at the shin directly below the knee. Stimulation electrodes may be positioned on the thigh above the sensing electrodes (not shown). The superior and middle sensing electrodes, as well as the inferior electrode, may be able to measure electrical signals that may be affected by the stimulation electrodes. In this embodiment the superior, middle, and inferior electrodes are aligned in a linear fashion. In some embodiments, they may be aligned to correspond to the direction of the underlying tendon. For example, one or more sensors may be aligned over a tendon to correspond to the direction of a signal traveling along the tendon. In some instances, this may provide an alignment that is substantially parallel to a longitudinal axis defined by the length of a straightened leg.

In this or alternative embodiments, at least one stimulation electrode is placed away from a sensing region and thus away from a sensing electrode. For example, a stimulation electrode may be placed at least 0.5 inches from a sensor. A stimulation electrode may be positioned over muscle and/or nervous tissue, while a sensing electrode may be positioned over a tendon (as opposed to the muscle and/or nervous tissue). Preferably, a sensor may be placed over a tendon corresponding to the muscle tissue stimulated by the stimulation electrode, such that the sensor may receive signals from the corresponding muscle and/or nervous tissue, the electrical pulses used to excite the muscle and/or nervous tissue, or both.

In use, one or more stimulation electrodes apply stimulation to the underlying muscle and/or nervous tissue, which causes the muscles to contract. The signal used to excite tissue or cause muscle contraction travels along the body away from the site of stimulation. This may include measurable signals traveling through or near the tendon. The electrical stimulating signals applied by the external source may be measured by the sensors at or near the location of the tendon. Changes in tendon tension, geometry, or other properties caused by the contraction of a mechanically connected muscle may alter signals traveling through or near the tendon, and the amount of change may be indicative of the degree of muscle contraction. Such signals may be measurable and useful (e.g. for optimization) at the tendon, even in a raw state (e.g., without amplification). This may provide advantages over traditional EMG systems which were measuring signals that would usually be too weak to be measured at that distance in a raw form (i.e. without amplification or use of a differential amplifier). This may also be advantageous for subjects with weak muscle interactions.

The sensors may be directly adjacent to one another with little or no spacing between them. For example, the sensors may be approximately 0.5 inches in diameter, so that when three sensors are placed next to one another, they take up about 1.5 inches. Alternatively, the sensors may be provided to have some spacing between one another. The sensors may have any dimensions (e.g., diameters of about 0.1 inches, 0.2 inches, 0.3 inches, 0.4 inches, 0.5 inches, 0.6 inches, 0.7 inches, 0.8 inches, 0.9 inches, 1.0 inches), and any number of them may be provided spaced at any distance apart.

The signals measured by the sensors along the length of the tendon may vary in amplitude and/or magnitude in accordance with the distance of the sensor from a stimulation electrode. For example, if a stimulation electrode is placed over a muscle on a thigh, and delivers an electrical stimulation signal, the signal may travel to the corresponding tendon and propagate along the length of the tendon. The sensor over the tendon that is closer to the stimulation electrode may measure the stimulation signal with a greater amplitude than a sensor that is further from the stimulation electrode since the stimulation signal may degrade along the length of the tendon.

In some embodiments, such as the embodiment in FIG. 1, a reference electrode placed below the knee can measure background electrical signals from the subject without measuring (or only minimally measuring) signals from the stimulation electrodes. The reference electrode may be at a sufficient distance from a stimulation electrode so as to substantially not measure a signal from the stimulation electrode. The reference electrode may be placed such that underlying anatomical features or intervening anatomical features may substantially prevent a signal from a stimulation electrode from being measured by the sensor. In some embodiments, the signals from the reference electrode(s) may be subtracted from the signals measured by other sensing electrodes to measure the activity in the sensing electrodes minus the natural electrical background.

In the exemplary embodiment shown in FIG. 4A, electrical signals measured at each sensing electrode may each first be processed individually using steps i)-iii) described above. Following this, the energy levels in the processed electrical waveform measured at each sensing electrode may be normalized by the strongest energy level (detected from the superior electrode) and compared. The normalization step is useful because it removes any dependency on overall waveform amplitude, which can be noisy or unreliable, for optimization of NMES. The strongest muscle contraction may induce the most tension and greatest geometry change on the tendon and surrounding anatomy, and thus produce the greatest amount of energy change (due to reflection, interference, and/or other factors) between the middle and inferior electrodes. Therefore, it is hypothesized that stronger contractions will produce response pulses with a relatively larger percentage of the original energy (as detected by the superior electrode) detected at the middle electrode and a relatively lower percentage of the original energy detected at the inferior electrode. Thus, one suitable algorithm to determine the pair or group of stimulation electrodes that produces the strongest muscle contraction would look for the largest difference in energy calculated at the middle and inferior sensing electrodes, respectively. Because only relative energies are compared, for this embodiment it may not be vital to ensure that the response pulse shapes (e.g., monophasic, biphasic, etc.) are similar prior to comparison. It is noteworthy that in this embodiment, the pair or group of stimulation electrodes selected as optimally located need not necessarily be the pair or group that produces the strongest overall energy amplitude as measured at any individual sensing electrode.

Figure 4B:
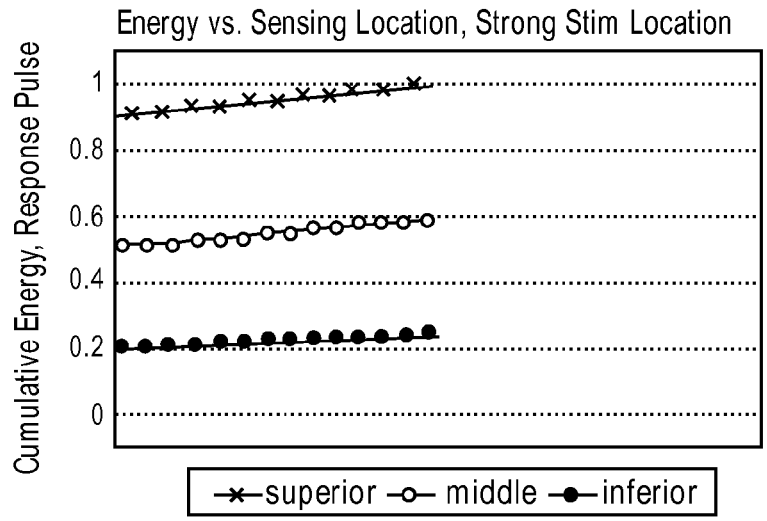
Figure 4C:
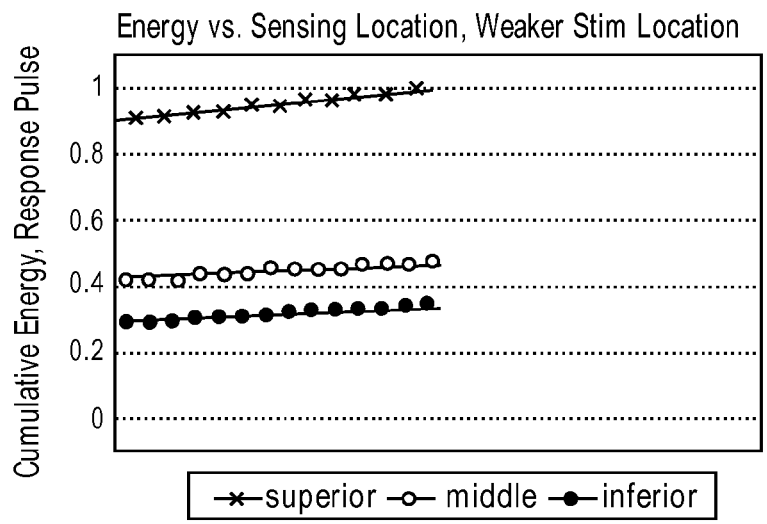

FIGS. 4B and 4C illustrate example plots of the cumulative energy contained in electrical activity sensed response pulses for muscle stimulation using the sensing electrodes in FIG. 4A that leads to a strong contraction shown in FIG. 4B a weaker contraction shown in FIG. 4C. The normalized cumulative energy plots (see steps i)—iii) described above) for a series of response pulses are shown for each of the three sensing electrodes for stimulation electrode pairs that may produce strong FIG. 4B and weaker FIG. 4C muscle contraction (and thus tendon tension). Shown are actual waveforms acquired by applying electrical stimulation to human quadriceps muscle and recording electrical activity data using the sensing electrode configuration shown in FIG. 4A. In FIG. 4B, the middle electrode records ~60% of the energy recorded by the superior electrode, while in FIG. 4C the middle electrode records ~55% of the energy recorded by the superior electrode. Similarly, in FIG. 4B the inferior electrode records ~25% of the original energy, while the inferior electrode in FIG. 4C records ~35% of the original energy. Comparing the two stimulation locations, FIG. 4B shows a 35% difference between middle and inferior electrodes, while FIG. 4C shows a 20% difference. This suggests a greater reflection, or a more constructive local energy interference, and thus a greater change in tendon tension and/or geometry, and thus a stronger muscle contraction in location 4B.

After the suitable signal processing algorithm, such as any of those described above, have analyzed the sensed signals and have automatically selected the optimally-located pair or group of stimulation electrodes in the array for energy delivery, a second optimization process can commence to adjust the energy level and/or waveform shape that may be used to induce muscle contraction during the course of NMES therapy. This could involve applying different signal processing algorithms to data collected during the initial series of default stimulation events, or the collection of new electrical activity data during a second series of preset stimulation events using only the ideal pair or group of stimulation electrodes. Although numerous strategies for energy adjustment are possible, it is believed that as the stimulation energy is moved from an inefficient amplitude to a sufficiently strong amplitude, there may be a large increase in the amplitude of the response pulses contained in the electrical activity waveform measured by the sensing electrodes. In a preferable embodiment, the average electrical current carried by the train of stimulation pulses may be increased until the large change in response pulse amplitude is detected. Further, the waveform shape could be adjusted based upon feedback from the electrical activity waveform. For example, if no large change in response pulse amplitude is detected, it could indicate that insufficient electrical energy may be reaching target muscles. In this scenario, it could be advantageous to employ the use of a sinusoidal (as opposed to biphasic square wave or other shaped) stimulation waveform, a waveform shape that has been shown to more effectively penetrate fatty tissue and other intermediate tissue layers that may lie between skin and muscle. As with previous stages of optimization, the NMES optimizations described in this paragraph may ideally be controlled by electronics, hardware, and/or firmware/software contained in the control unit. In alternate embodiments, portions or all of the controlling technology may be contained on the stimulation or sensing pads.

In another embodiment, sensing electrodes configured similarly to the setup shown in FIG. 4A may be used. Alternatively, additional configurations (such as those that use three or more electrodes in the tendon region) of sensing electrodes could be used without loss of generality. In this variation, each sensing electrode may record signals relative to a ground electrode (located, for example, over lower knee, shin, or other bony prominence) without the use of a differential amplifier. Accordingly, signals recorded during stimulation may generally be reflective of the stimulation pulses applied to the person, as circuitry may not be sufficiently sensitive to accurately record the response pulses that arise from electrical activity components produced by the muscle contraction. Benefits to this variation may include i) signal processing advantages associated with larger signal amplitude (stimulation pulses relative to EMG response—i.e., no need for amplification that may add noise, ii) improved performance in persons with low EMG strength or poor conduction of EMG signals to surface electrodes, and iii) consistent shape of recorded signals from the tendon region (ex. no need to detect whether recorded response pulses are monophasic, biphasic, etc.).

In a preferable embodiment of the devices, systems and methods presently-disclosed, the stimulation control unit automatically selects one or more locations to deliver energy to the body using feedback from the sensor(s). In one implementation of the embodiment, during a calibration period stimulation signals with the same energy intensity are transmitted to the body through different pairs or groups of electrodes in a pre-configured or configurable array. During each energy transmission event, data are captured by the sensors and transmitted to the control unit, where it can be temporarily stored in memory. After a default number of stimulation events have taken place, algorithms executed by the control unit will use the sensor data to identify the most efficient pair or group of stimulation electrodes to utilize to deliver energy to the user (as defined as the pair or group of stimulation electrodes leading to the strongest muscle contraction, as measured by the sensor). Muscle stimulation may subsequently be primarily delivered through this ideal pair or group of stimulation electrodes during the remainder of the therapy session. Following this identification of the ideal pair or group of stimulation electrodes, further calibration steps may occur or the device may exit a calibration mode and transition, for example, to a therapy mode where it delivers NMES to the user for the desired treatment period. In alternate implementations of this preferable embodiment, several or all of the electrode pairs or groups in a pre-configured array are used simultaneously to deliver electrical energy, independently of one another or in parallel, to the body. Algorithms that are applied to sensor data captured during calibration periods are used to adjust the relative energy intensity, phase delay, or other properties of the stimulation energy transmitted by the control unit. In alternative embodiments, no distinct calibration phase is utilized and all optimization steps are made 'on-the-fly' during the treatment process. The devices and systems of the present disclosure are capable of carrying out the calibration steps associated with this preferable embodiment.

In some embodiments, the devices and systems disclosed herein will be capable of automatically optimizing one or more stimulation parameters using data collected by tendon sensors. In a preferable embodiment, this process may begin with the optimization of stimulation energy intensity based upon the needs of the user during the current treatment session. The disclosed devices and systems will be capable of selecting an energy intensity for use that produces a strong muscle contraction that is both well-tolerated (in terms of patient discomfort, or in sedated or otherwise non-interactive patients, as inferred from vital signs such as heart rate, respiratory rate, blood pressure, etc.) and safe for use. The devices and systems shall be able to identify and deliver energy intensities greater than that associated with onset of visible muscle contraction without extended interaction time from an operator. In one implementation of the embodiment, the operator needs only to place stimulation and sensor pads (or, alternatively, discrete stimulation electrodes and sensor(s)) and then press a single button on the control unit to initiate the process of self-optimization followed by delivery of optimized therapy. In a variation of this embodiment, the operator may be able to select gross amplitude settings (for example, two buttons or a toggle switch or equivalent allow for the selection of 'high' or 'low' intensity), and the devices and systems will optimize energy intensity within a predefined range associated with the gross amplitude setting selected.

FIGS. 5A-5E illustrate several exemplary arrangements of a stimulation pad (103) that contains stimulation electrodes (101) that may be used to deliver energy to the body. FIGS. 5A-5E illustrates various examples for the configuration of electrodes into an array or arrangement on a stimulation pad. Pair or groups of electrodes may be pre-configured to be in communication with one another (e.g., those identified in 102) or may be configurable by the control unit prior or during NMES therapy. Stimulation pads and electrode configurations may vary considerable in shape depending on the body part intended for NMES treatment. FIG. 5F illustrates a stimulation pad containing electrodes from a top-view on a body part (104) of a user. FIG. 5G illustrates a stimulation pad containing electrodes from a side or profile view on the body part of a user. In preferable embodiments, the stimulation pad may be thin, soft, and flexible.

FIG. 6A illustrates a preferable embodiment of an exemplary system that includes a stimulation pad (202) and a sensor pad (203) secured to the body part of a user (201). The system can be used in any of the applications described herein, such as using tendon signals in the automatic optimization of stimulation parameters. Stimulation and sensor pads are connected via a wire or cable to a control unit (204). FIG. 6B(i)-(ii) shows a top and side views of one embodiment of a sensor pad comprising both a primary (205) and a reference/ground (206) sensor. Sensor pad also contains a marker (207) that facilitates proper and rapid placement by an operator. FIG. 6C illustrates an implementation of a sensor pad using four primary tendon sensors without a reference or ground sensor built into the sensor pad. FIG. 6D illustrates an implementation of sensor pad that uses a central circular geometry to facilitate placement and contains both primary and reference sensors. The sensor pad shown in FIG. 6E is similar to that shown in FIG. 6D, but does not contain a reference sensor. FIG. 6F illustrates an implementation of a sensor pad using multiple sensors and arrow markings to facilitate placement. FIG. 6G illustrates a second implementation of the system on the body of a user.

FIGS. 7A-C illustrate an exemplary embodiment of a system and method of use. The system can be used in any of the applications described herein, such as using tendon signals in the automatic optimization of stimulation parameters. FIGS. 7A(i)-(ii) illustrate discrete electrodes (304) placed over the muscle of both leg 1(301) and leg 2(302) of a user. Discrete tendon sensors (305 and 306) are placed over the quadriceps tendons (303) of the user. In this implementation, only one sensor is required per muscle group receiving NMES. NMES energy delivery locations and/or stimulation parameters are optimized by first providing energy to leg 1 (as described in FIG. 7C). During this period, leg 2sensor (306) serves as a ground for leg 1 sensor (305). NMES may be optimized completely on one leg before reversing the process to optimize parameters on the other leg, or stimulation energy and data collection may be alternated between the legs during the calibration process. Following calibration, energy may be delivered to both legs simultaneously or continue to be provided to one leg at a time. FIG. 7B(i)-(ii) illustrates a variation embodiment using four total sensors where the reference sensor for leg 1 (306) is placed on the knee of leg 2. The reference sensor for leg 2(307) is placed on the knee of leg 1. Similar steps in the method may be executed for calibration.

FIGS. 8A-8D illustrates several example implementations of a preferable embodiment that features stimulation and sensor pads that have coordinating or complementary geometries. The pads can be used in any of the applications herein. Solely by way of example, in this figure configurations are shown for placement on the thigh of a user. Other geometries designed using the same underlying concept will be appropriate for different anatomical regions. In FIG. 8A, a sensor pad (401) is designed with a large circular component intended to be placed on the knee (403) of the user. The sensor pad contains a protrusion portion which extends superior to the knee and contacts the body over the quadriceps tendon. The tendon sensor is contained in this region of the sensor pad. The stimulation pad (402) contains an appropriately shaped notch intended to fit around the protrusion portion of the stimulation pad. This geometry ensures that the stimulation pad is placed both at a correct angle on the leg and also is located at a suitable distance from the knee. The relative positions of the sensor and stimulation electrodes are also now fixed with a greater degree of precision, which may improve the reliability of sensor data and subsequently system performance.

FIG. 8B illustrates a second implementation of a preferable embodiment that uses stimulation and sensor pads with geometries and markings that allow for rapid correct placement. The sensor pad (401) spreads laterally across the leg at the height of the tendon, and contains a concave lower region to 'cup' or conform to the knee cap. Arrows on the sensor pad are intended to be aligned with complementary arrows on the stimulation pad such that the stimulation pad is placed at the proper angle and at the proper lateral location. The material length of the pad ensures electrodes remain at a desirable distance from the knee. FIG. 8C shows a third example of stimulation and sensor pads where the sensor pad takes on a triangular geometric shape and fits into a complementary-shaped notch in the stimulation pad. FIG. 8D shows a fourth example implementation where the stimulation pad physically sits atop a portion of the sensor pad and may be fixed in position through the use of snaps, Velcro, or other similar connectors (404).

Figure 9B:
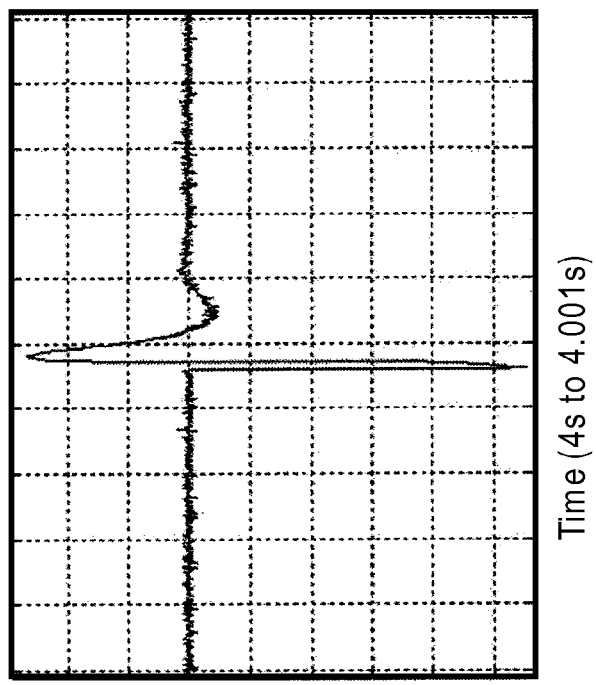
FIGS. 9A-B illustrate a tendon signal captured from a human volunteer receiving NMES.
Figure 9A:
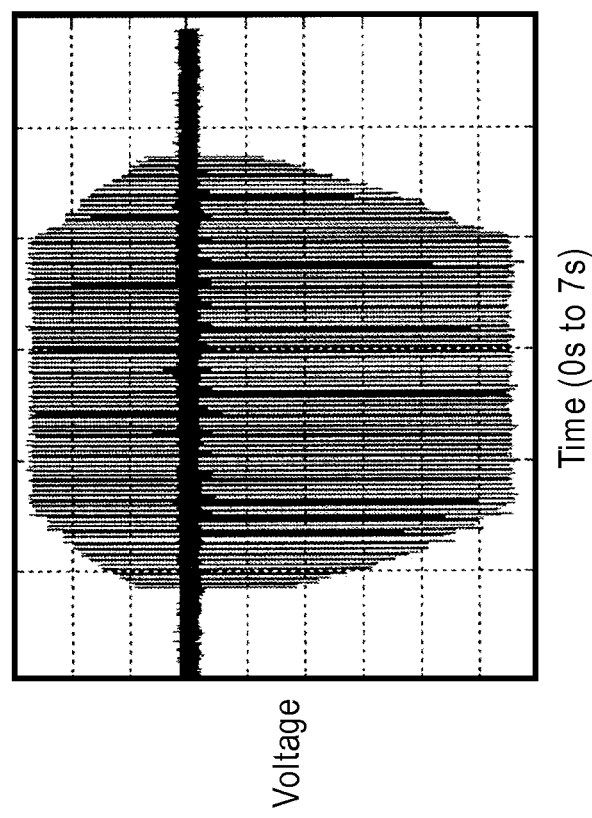

FIGS. 9A-B illustrates a tendon signal captured from a human volunteer receiving NMES with a preferable embodiment of the system. The voltage signal was captured by an electrical tendon sensor using a second ground sensor placed away on the body at a region remote from the NMES stimulation. Sensor data acquisition was synchronized to the delivery of NMES, with data sensing starting approximately 1 second before and ending approximately 1 second after the delivery of the 5 s train of stimulation energy, as shown in FIG. 9A. Voltage data recorded by the sensing electrodes originates at least in part from the pulsed stimulation energy delivered to the user from the control unit. In this example, the 5 s train of stimulation pulses applied to the user contained 1 s energy ramp-up and ramp-down periods, so peak energy intensity was applied for the middle 3 seconds of stimulation. This 5 second period represents one stimulation event that leads to one muscle contraction-hold-release cycle. During this cycle, many (in this example, 200) stimulation pulses are supplied intermittently to the user. A zoom-in view in FIG. 9B shows the sensed tendon signal that is time-correlated with one of these stimulation pulses is provided. In this embodiment captured voltage signals have the same general shape and polarity as stimulation signals applied to the stimulation electrodes closest in proximity to the sensor(s). For example, the total sensed signal provided in FIG. 9A is in part composed of energy originating from the many individual pulses which are sent to stimulation electrodes and detected by the sensor(s) a very short time later (see zoom-in in FIG. 9B). Because tendon signals are captured during the time when many individual stimulation pulse events are delivered by the control unit during a muscle contraction-and-hold period (in some cases, a single period), subtle changes in tendon impedance and/or geometry may be extracted by applying signal processing techniques to this large data ensemble. For example, voltage amplitude, average sensed pulse width, changes in amplitude or pulse width, average amplitude variation, change in parameters between two or more sensors, and other signal characteristics may be analyzed.

In preferable embodiments, the control unit or sensor pads or both will include electronic hardware, software, or both capable of accurately measuring tendon sensor data. For embodiments and configurations that involve the use of electrical tendon sensors that produce signals similar to those illustrated in FIGS. 9A and B, hardware components may include analog-to-digital converters with reasonably high sampling speed (ex. 20-100 kHz sampling) and resolution (ex. 10-12 bit). Electrical voltages may be made relative to a signals sensed by a reference or ground sensor or may be made relative to a ground (floating or otherwise) not in contact with the body (for example, in the control unit). In some embodiments, no amplification or differential amplification (techniques typically required during EMG) is necessary for signals to be captured accurately and be suitable for signal processing. Sensing periods may be synchronized or otherwise timed to correspond to discrete windows of time when stimulation energy is applied to the body.

In a preferable embodiment, the control unit is capable of transmitting stimulation pulses on at least one and preferably many more (e.g., 8-20) channels simultaneously and independently. In many cases, applying current to two or more pairs or groups of electrodes independently is advantageous to simply splitting the current from a single channel across two or more parallel electrode configurations. In the situation where current from a single channel is split (i.e., two or more electrode pairs receiving the signal are not receiving independent energy signals) between two or more electrode pairs or groups, equal distribution of the original energy is not guaranteed. For example, without wishing to be bound by any theory, it is believed that if 40 mA of supply current is split between two electrode pairs, perfect balancing of electrical impedance between each electrode pair is required if 20 mA will travel along each route. This situation of balanced impedance pathways is unlikely to occur in vivo. In addition to the ability to transmit stimulation pulses on independent channels simultaneously, some embodiments of the control unit are also capable of creating arbitrary phase delays between pulses originating from different channels.

In a preferable embodiment, the stimulation and sensor pads are comprised of a thin and flexible housing with an adhesive hydrogel backing to facilitate maintenance of skin contact with the person receiving NMES. The hydrogel backing will also enhance the coupling of electrical energy and signals between stimulation electrodes and sensors and the person's body. Hydrogel backing may be used in discrete regions to allow for skin adhesion, for example in the regions including electrodes and sensors, or in larger regions. The stimulation pad contains two or more strategically-placed surface electrodes that are used to deliver electrical energy to muscles and/or nerves in order to produce muscle contraction. The sensor pad contains at least one sensor that is strategically-placed to be specifically located, for example in the vicinity of the tendon that is mechanically-coupled to the muscle group being stimulated and also in a suitable location relative to the stimulation electrodes. In a preferable embodiment, a tendon sensor is an electrical sensor that is capable of extracting electrical signals from the body. In variations of a preferable embodiment, the tendon sensor is a non-electrical sensor, an electro-mechanical transducer, or other suitable measurement mechanism that measures tendon tension, geometry, and/or impedance (or relative changes in these parameters).

In some embodiments, the stimulation electrodes are arranged on a stimulation pad in an array with a predetermined layout (see, for example, FIGS. 5A-E). In some embodiments, the stimulation electrodes are arranged in a configurable array. The array may be configurable such that, at any given time, only a subset of the electrodes in the array may be actively delivering energy to a person receiving NMES. However, electrodes inactive for energy delivery may still be configured to deliver relevant information (such as the electrical impedance between it and a second electrode in the array) to the control unit. In a variation embodiment, the stimulation pad may contain only 2 stimulation electrodes, with both electrodes being active during NMES energy delivery. In another variation embodiment, the surface electrodes may not be contained in a larger stimulation pad. Instead, discrete electrodes of any size or shape could be utilized by an NMES operator and placed in the position deemed by the operator to be most suitable.

In some embodiments, at least one sensor is integrated into a sensor pad. The sensor pad can contain features or markings that assist an operator in its suitable placement, for example in an anatomic region in the vicinity of the desired tendon (see FIG. 6G). In preferable embodiments the sensor pad will contain a single electrical sensor that contacts the skin surface, for example a sensor similar to those used during EMG or EKG data collection to extract electrical signals from the body. In this embodiment, two or more sets of stimulation and sensing pads may be utilized during a treatment session (see FIGS. 7A-B), for example if during a treatment session both legs or both arms were to receive NMES therapy. In this configuration, following the example of quadriceps stimulation in FIGS. 7A-B, stimulation current is applied to one leg at a time during a calibration phase of NMES treatment. During energy delivery to a first leg, the tendon sensor on that leg receives electrical signals that at least partially originate from energy delivered by the control unit to the stimulation electrodes, while the tendon sensor on the second leg may serve as a ground channel or reference sensor for the sensor on the first leg. This process allows for calibration of energy delivery and/or other parameters on the first leg. To calibrate energy delivery and/or other parameters on the second leg, the process is alternated between legs or reversed upon completion of calibration in the first leg. Once the calibration phase is complete, NMES may be delivered to both legs simultaneously or may alternate between legs with or without further use of the sensors. This embodiment of the system and method is particularly useful because (1) it minimizes hardware requirements associated with data recording, sampling, and related tasks and (2) it minimizes the complexity of the system setup that must be undertaken by the operator, reducing the time requirements of delivering NMES.

In a second preferable embodiment, the sensor pad may contain both a primary sensor and also a reference or ground sensor in the same pad. Generally, the ground sensor will be intended to be placed over a bony prominence and may be as remote as conveniently possible from the primary sensor. As an example, in the case of quadriceps stimulation, the primary sensor may be a tendon sensor that sits on the skin surface over or around the quadriceps tendon, while the ground sensor may be located distally on the skin surface over the knee cap area. In a variation of this embodiment, the ground sensor may be an independent entity that is placed separately from the sensor pad, allowing it to be placed even more remotely from the primary tendon sensor (for example, on the surface of the skin near the shin). In another variation of this embodiment, both the primary tendon sensor and the reference ground sensor are discrete components that are not contained on a sensor pad and are placed independently in the locations deemed most suitable by the operator. In a third variation of this embodiment, 2 or 3 or more sensors are integrated into the sensor pad to capture signals from the tendon region, and an additional ground or reference sensor is located elsewhere in the sensor pad or somewhere further remote on the body (for example, as a separate sensor on the shin or as a sensor built into a second sensor pad that contacts the body at a second anatomic location).

In a preferable embodiment, the stimulation and sensor pads have suitable geometries to facilitate proper placement relative to muscle/tendon regions and to one another. This inventive feature will be particularly useful during stimulation of the thigh muscles (e.g., quadriceps, hamstrings, gluteals) and muscles of the core, where few anatomical markers exist to facilitate proper placement. In one example (see FIGS. 8A-D), the sensor pad is fitted to make use of the knee cap as a readily-identifiable anatomical marker. In FIGS. 8A, C, and D, the sensor pad contains a protrusion (i.e. 'male' part) to guide the placement of a stimulation pad that contains a complementary notch (i.e. 'female' part). This notch/protrusion alignment assists to constrain deviations from the ideal placement distance between the stimulation electrodes and the sensors, and also ensures that the stimulation electrodes are aligned at a suitable distance from the knee and at the appropriate orientation angle. Essentially, this design extends the utility of the anatomical marker of the knee to assist placement of pads in a region where no easily-identifiable anatomical markers are available. Other implementations of this preferable embodiment will use other mechanisms (e.g., snaps, straps, wired connections, etc.) to improve accuracy in both the relative and overall placements of the stimulation and sensor pads.

Figure 10A:
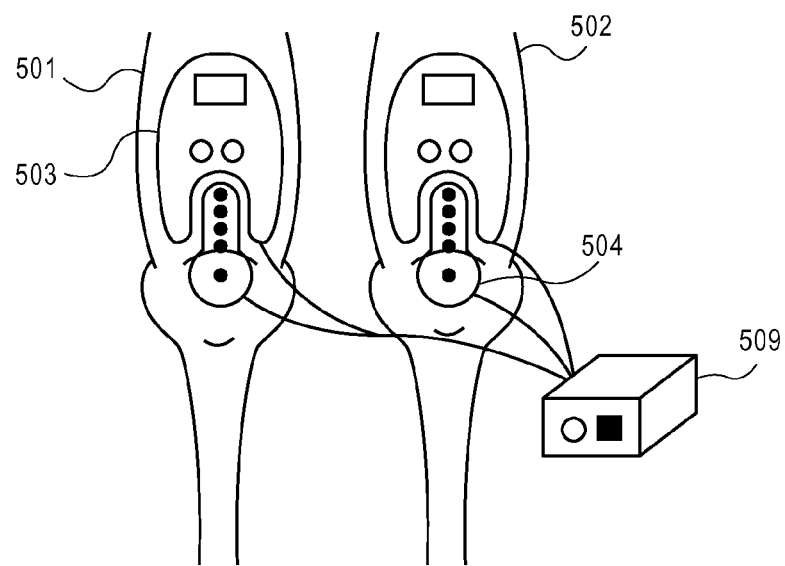
FIG. 10A illustrates an exemplary muscle stimulation system.
Figure 10B:
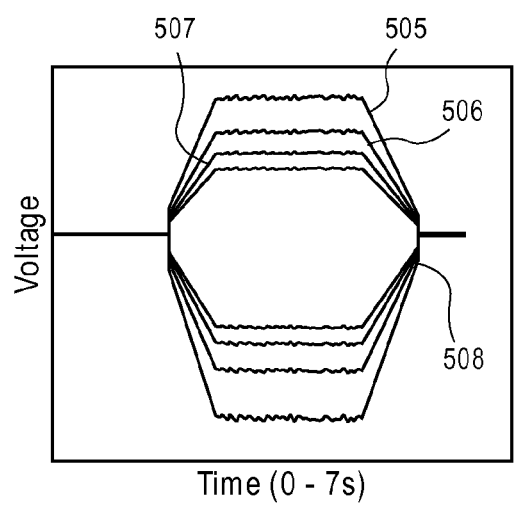
FIG. 10B illustrates an example set of sensed voltage.
Figure 10C:
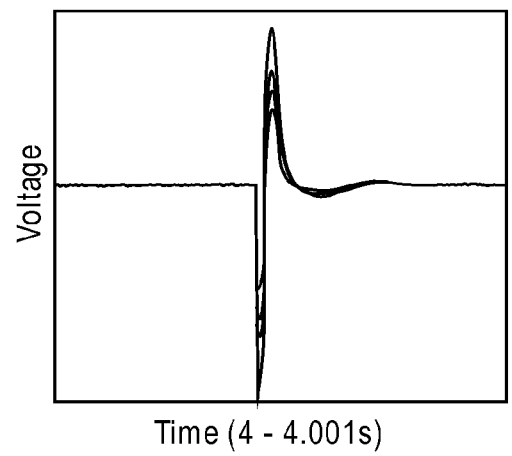
FIG. 10C shows a zoom-in view from FIG. 10B.

FIG. 10A illustrates a variation of a preferable embodiment that involves the use of a sensor pad with four tendon sensors and a reference ground sensor. In this example, NMES is applied to both of a user's legs, and stimulation pads (503) and sensor pads (504) are placed on both leg 1(501) and leg 2(502) of the user. In this embodiment, each sensor and stimulation pad connect separately to a control unit (509). FIG. 10B illustrates an example set of voltage acquired in a similar fashion as described above in the description of FIG. 9. Shown are 4 time-registered, voltage signals (505-508) corresponding to the 4 sensors included in the sensor pad. Signals are overlaid on top of one another to demonstrate similar shape but different average amplitude. FIG. 10C shows a zoom-in showing the sensed tendon signals that are time-correlated with one of the stimulation pulses sent by the control unit to electrodes in the stimulation pad. Without wishing to be bound by any theory, it is believed that the amplitude of the voltage signal detected by each sensor is a function of both distance from the stimulation electrodes (source of energy) and tendon characteristics, including impedance and geometry. It is further believed that, for the case of the leg being fully or nearly-fully extended prior to contraction (as in case of bed-bound patient), relative distances between sensors and electrodes change little during contraction, and that non-significant error is introduced by assuming that this small change in vector-distance between sensors and electrodes during contraction is identical for all four sensors. In this example, the average difference, across the entire data ensemble, between the peak values of detected voltage spikes may be used to describe the state of the tendon, and through proxy the relative state of muscle contraction. As a functional example, the presently-described signals may be captured as the control unit automatically cycles through muscle stimulation events delivered by different pairs or groups of stimulation electrodes. Sensor data are automatically captured and analyzed by looking for largest ensemble voltage differences, and an ideal location for energy delivery is automatically-determined. In variation embodiments, sensor signals may be normalized or scaled prior to analysis, or other signal characteristics, such as proportional changes in peak measured energy or deviations in ensemble-average pulse width, may be analyzed.

In variations of the preferable embodiment, sensors are used to capture data from both sub-threshold (i.e., energy intensity not sufficiently strong to produce appreciable muscle contraction in the target region of tissue) and super-threshold muscle stimulation energy intensities. Data are then automatically compared using software analysis techniques as described above to optimize at least one aspect of muscle stimulation. Some embodiments may use reference sub-threshold sensor data to improve calculation accuracy when analyzing sensor data from one or more super-threshold stimulation events. In some implementations, parameters are optimized by incrementally adjusting stimulation pulse waveforms applied to the user until the output of an analytical step arrived at through application of signal processing techniques to captured tendon data reaches or exceeds a threshold value. In some embodiments, this threshold value may be empirically determined a priori through human evaluations. In alternative embodiments, this threshold value may be calculated on a per-user or per-session basis given information available from that particular NMES therapy session (e.g., impedance between stimulation electrodes, user's age, user's body-fat percentage, amplitude of voltage waveforms detected by tendon sensors, etc.). In some embodiments, a combination of newly-calculated and empirical data may be utilized to determine threshold values implemented during the optimization process.

In some variations of a preferable embodiment, mathematical calculations may be applied to sensor data collected during sub- and super-threshold stimulation events to assist in automatic optimization of stimulation therapy. For example, it can be reasonably assumed that the amplitude characteristics of voltage traces recorded by sensing electrodes during sub-threshold and super-threshold stimulation, respectively, can be described by:

$$V_s \propto I_s Z \quad (1)$$

$$V_c \propto I_c Z + M \quad (2),$$

where $V_s$ and $V_c$ describe voltage signals resulting from each stimulation pulse during sub-threshold and super-threshold contraction, respectively, $I_s$ and $I_c$ describe current delivered by the stimulation electrodes during sub-threshold and super-threshold contraction, respectively, Z is the electrical impedance between the electrode pair or group used for stimulation, and M is a term describing the effect of tendon tension and/or geometry changes and/or other factors related to muscle contraction on the recorded signals. In Equation (2), the parameter M is modeled as an additive term; those skilled in the art will recognize that minor variations of Equation (2) and subsequent processing steps could incorporate the parameter M as a multiplicative term, exponential term, or several other mathematical representations.

Continuing the analysis above, $V_s$ and $V_c$ are known through measurement of sensor data and $I_s$ and $I_c$ are known through measurement of control unit output. Although Z may be measured, for instance measured by the control unit through electrode contacts, it is a complex characteristic containing both real and (mathematically-speaking) imaginary components. Therefore it may be advantageous to solve for M instead through combination of other known parameters:

$$M = ([(V_c/V_s) - (I_c/I_s)] \times V_s) \quad (3).$$

Subsequent steps carried out automatically by the control unit may seek to optimize parameters most efficiently through analysis of calculated parameter M. In one implementation, the pair or group of electrodes that produced the largest value of M for a given $I_c$ is selected for use during therapy. In a second implementation, the pulse width, energy intensity, or pulse repetition rate (or some combination of the three) is optimized by determining which parameter settings produce a value for M that is most desirable.

In some exemplary methods, sensed signals are examined over many pulse cycles such that small differences or trends can be combined or analyzed with improved signal-to-noise ratio. For example, custom software programs measure how the peak voltage amplitudes (maxima, minima, or both) of individual pulses contained within an ensemble of sensor data captured during a stimulation event change over the course of the ensemble (i.e., through time). Methods including single or multi-order least squares regression, fixed-window amplitude comparison, or other suitable techniques may be utilized to estimate the magnitude of any changes over time with an adequate level of accuracy. Without wishing to be bound by any theory, it is believed that stronger muscle contractions will induce greater anatomical or physiological changes during the measurement period when the ensemble data are recorded (i.e., during the period the applied stimulation energy is causing the muscle to transition from a relaxed state to a contracted state) than weaker muscle contractions. For example, when using a tendon sensor, changes in tendon impedance and/or geometry (and the respective electrical impacts thereof) are expected to be more significant during strong muscle contraction. These larger changes will lead to greater changes in measured voltage, and thus this voltage-energy relationship can be a valuable parameter through which to optimize muscle stimulation parameters and/or energy delivery locations.

In a preferable implementation, sub-threshold stimulation energy intensities are applied to the body to capture voltage data during periods where little to no muscle contraction takes place. One or more higher energy intensity stimulation events follow, during which time additional sensor data are acquired, and additional calculations are made using voltage data (for example, voltage amplitude changes over time during contraction). In one implementation, the energy intensity utilized during NMES therapy is increased until a threshold degree of change is reached. This threshold may be predetermined or it may be dynamic based upon external factors. For example, given the results of calculations garnered from sub-threshold contraction data, a dynamic or proportional threshold of change may be chosen which represents the amount of change in sensor data thought to be most representative of optimal muscle contraction and/or stimulation parameters. This method can be employed using software applied to electrical sensor data, for example tendon sensors or similar sensors placed in non-tendon anatomical regions, or to data from mechanical sensors such as accelerometers. In a variation of this implementation, multiple sets of sensor data are acquired at each stimulation energy intensity utilized in order to improve accuracy through averaging, correlation, criteria-based rejection, or other signal analysis techniques. Those skilled in the art will recognize that the above example is just one of a multitude of signal processing techniques that can be applied to analyze data as described herein.

Preferable embodiments of the presently-disclosed devices, systems, and methods may have robust sensing and optimization capabilities that may help account for varying patient characteristics or physiology. As an illustrative example, readings on the sensors may be coupled with software or other mechanisms governed by the control unit to determine the relative level of tissue edema in a patient. Without wishing to be bound by any theory, it is believed that significant edema will alter the electrical impedance of target tissues in a measurable way that can be detected through sensors that record and analyze voltage measurements during stimulation. These detection algorithms may make use of single intensity sensor data or may alternatively utilize sensor data acquired during periods of stimulation at two or more intensities. In variation embodiments, alternative sensors may be coupled to the system described herein to detect and estimate edema, for example pressure sensors or indentor systems with sufficient sensitivity to mimic the pitting test typical performed manually during edema assessment. These edema detecting capabilities may be extremely useful for proper optimization of an effective therapy, for example, because edematous patients typically require higher intensity stimulation to achieve suitable muscle contraction relative to non-edematous patients. Setup times may also be shortened, as lower intensity stimulation attempts may be bypassed in an optimization algorithm if it is suspected that high intensities are required.

Preferable embodiments may also augment data from tendon-based sensors with information from additional sensors. For example, motion sensors or accelerometers may be integrated into a stimulation pad. In this example, these sensors are not intended to measure muscle reactions from stimulation, but instead are intended for use as a way to validate the quality of data acquired via primary sensors. For example, some patients confined to bed rest experience conditions like tremors or shaking that may prevent accurate 'resting state' measurements of tendon tension and/or geometry from being recorded. In these patients, improved performance may be achieved if non-stimulation-based muscle movement can be detected and accounted for through software or other mechanisms deployed by the control unit.

Following automated optimization and self-calibration, the control unit may automatically initiate energy delivery to the person receiving NMES. NMES may continue for a predetermined amount of time that is either specified by the operator or internally set by the control unit. Under normal modes of operation, energy delivery may terminate automatically following this predetermined period of time and provide an alert in the form of a sound, light, text message, other visual indicator, or other suitable mechanism to the operator. Alternatively, energy delivery can be terminated early under normal operating conditions by an operator or another person pressing an emergency shutoff button, knob, dial, switch, or other control on the control unit.

In yet other embodiments, the stimulation pads may contain only two stimulating electrodes, with one electrode serving as the 'reference' electrode. In this mode of operation, the operator may initiate therapy by pressing a button on either the stimulation pad or the control unit or by performing another action. The control unit may automatically optimize electrical stimulation parameters given feedback from the sensor element(s) in the pad, then initiate therapy automatically. In a variation of this embodiment, the control unit may simply initiate NMES therapy automatically using a default set of parameters using no optimization.

Another embodiment of a NMES system could involve a stimulation pad without any sensor element(s). In this mode of operation, the operator would apply the stimulation pad to the target muscle and press a button on the control unit or stimulation pad or perform another suitable action. The control unit could automatically optimize features of the NMES therapy based upon information available from the stimulation electrodes. One example of this information is the electrical impedance sensed between active or non-active stimulation electrodes.

Some of the embodiments above generally describe an electrical tendon signal indicative of a state of a tendon. In some embodiments the sensed signal is a non-electrical signal indicative of a state of a tendon. The state of the tendon includes changes in tendon tension, geometry, and/or electrical impedance. For example, an indenter-based system or non-contact imaging technique such as ultrasound-based elastography may be used to assess tissue stiffness in the anatomic region of the tendon, which is used to measure tendon tension. Non-compressible elastic materials such as tissue stiffen under mechanical strain. In an alternative embodiment a magnetic or inductive sensor is used to detect electrical impedance changes non-invasively without relying on the direct extraction of electrical signals from the body. Alternative preferable embodiments that make use of non-electrical-based tendon sensors will comprise hardware and/or software components suitable for the sensor system in use. For example, a system implementing an ultrasound-based elastography technique to infer tendon tension through its mechanical stiffness may contain piezoelectric sensors, beam forming/focusing hardware and/or software, and analog-to-digital converters suitable for signals in the ultrasonic frequency range (for example, sampling at 20-100 MHz) or pre-demodulated frequency range.

The disclosure herein also includes systems that do not sense signals that are indicative of a state of a tendon to optimize muscle stimulation parameters. In these embodiments the systems and methods are similar to those described above with respect to tendon signals. For example, the non-tendon sensors sense electrical energy that is delivered to the body by an external source. The sensors are outside of the stimulation region. Signals measured by sensors are reflective of the degree of muscle contraction induced and thus information from the sensors is used to optimize one or more parameters related to NMES therapy. In these systems and methods, sensors measure electrical energy delivered to the body during NMES at locations proximal to but at some distance (ex. 1-10 cm) from the NMES delivery site(s). Signals captured by sensors are similar to those shown in FIG. 9 but lack the influence of tendon tension and/or geometry and are instead influenced by other factors, such as the varying impedance of a bulkening muscle, the varying proximity to a dynamic structure (such as an elevated patella), a blood flow velocity boost from muscle contracting around vessels, or other events. As one example, without wishing to be bound by any theory, it is believed that as a muscle contracts its anisotropic fiber structure shifts as it bulkens. This structural anatomical change alters available electrical conduction paths and impacts how applied stimulation signals are distorted as they travel away from a stimulation region. As a second example, blood flow carries charged particles and ions that may create an electromagnetic field. As muscles contract around a vessel, blood flow velocity may increase in a manner related to contraction strength, changing the amplitude and/or shape of an induced electromagnetic field which can be sensed by a properly configured sensor system. Nearly identical processing techniques are applied to the sensed data to achieve the objectives previously outlined.

In some embodiments sensors detect electrical signals applied remotely to the body during the stimulation period(s), but detected electrical signals are distinct or independent from the NMES signals used to produce muscle contraction. For example, some embodiments use a higher-frequency signal simultaneously-applied with the NMES signals and use a sensor/detection system configured to filter or eliminate sensed NMES components while retaining the higher frequency signals for analyses related to NMES optimization.

In some embodiments sensors are configured to specifically note changes in patellar elevation during stimulation of the quadriceps muscles. Strain gauges, accelerometers, distance sensors (ex. ultrasound/radar distance sensors), magnetic, optical, or similar sensors may be implemented to detect changes in the patella's position during periods of muscle contraction. Patella position (or changes in position from a non- or minimally-contracted state) are indicative of the degree of muscle contraction induced in the quadriceps muscles. In some embodiments, one each of a pair of sensors may be integrated into stimulation and sensor pads, respectively, which are not mechanically-connected.

What is claimed is:

1. A method of electrically stimulating muscle, comprising:
   applying a first electrical stimulating signal from an energy source to a muscle at a stimulation region;
   sensing an electrical signal in a sensing region that is away from the stimulation region when applying the first electrical stimulating signal;
   adjusting at least one parameter of the first electrical stimulating signal based on the sensed electrical signal; and
   applying a second electrical stimulating signal from the energy source to the muscle, wherein the second electrical stimulating signal comprises the at least one adjusted parameter.

2. The method of claim 1 wherein sensing an electrical signal comprises sensing the first electrical stimulating signal, or a change that occurs in the first electrical stimulating signal between the stimulation region and the sensing region.

3. The method of claim 1 wherein sensing an electrical signal comprises sensing an electrical signal independent of or multiplexed into the first electrical stimulating signal, or a change that occurs in the independent or multiplexed signal between the stimulation region and the sensing region.

4. The method of claim 1 wherein the first electrical stimulating energy signal has a general waveform shape and the sensing step comprises sensing an electrical signal with the same general waveform shape.

5. The method of claim 4 wherein the first waveform is biphasic and the sensing step comprises sensing the biphasic signal.

6. The method of claim 5 wherein the sensing step comprises sensing a biphasic signal with the same phase distribution and approximately the same pulse width as the first waveform.

7. The method of claim 1 wherein the method further comprises using a control unit to analyze the peak voltage amplitude of the sensed signal, and wherein adjusting the at least one parameter of the electrical stimulation energy is based on analyzing the peak voltage amplitude of the sensed energy.

8. The method of claim 1 wherein the applying step comprises applying a first electrical stimulating signal with a first energy intensity, the method further comprising determining if the sensed electrical signal satisfies a threshold for adequate muscle contraction, and if so, the method further comprises delivering muscle stimulation therapy with a stimulating signal that comprises the first energy intensity.

9. The method of claim 8 wherein if the sensed electrical signal does not satisfy the threshold for adequate muscle contraction, applying the second electrical stimulating signal with an second energy intensity greater than the first energy intensity, and further sensing an electrical signal during the time when the second electrical stimulating signal is applied, and determining if the second electrical stimulating signal satisfies a threshold for adequate muscle contraction.

10. A muscle stimulation system, including:
    at least one stimulating electrode adapted to apply a stimulating electrical signal to a muscle at a stimulation region;
    at least one sensor adapted to sense the stimulating electrical signal or a change in the stimulating electrical signal at a sensing region; and
    a control unit adapted to analyze the sensed stimulating electrical signal or a change in the stimulating electrical signal that occurs between the stimulation region and the sensing region.

11. The system of claim 10 wherein the control unit is adapted to modify at least one parameter of the stimulating electrical signal, deliver a second stimulating electrical signal to the at least one stimulating electrode with the modified parameter, and compare a second sensed stimulating electrical signal with the sensed stimulating electrical signal.

12. The system of claim 10 wherein the control unit is further adapted to determine which of the second stimulating electrical signal and the stimulating electrical signal results in a more efficient muscle contraction.

13. The system of claim 12 wherein the control unit is adapted to automatically deliver a muscle stimulation therapy to the muscle with either the second stimulating electrical signal or the stimulating electrical signal depending on which results in a more efficient muscle contraction.

14. The system of claim 10 wherein the control unit is adapted to analyze the peak voltage amplitude of the sensed stimulating electrical signal.

15. The system of claim 10 further comprising a stimulation pad comprising the at least one stimulating electrode, and a sensing pad comprising the at least one sensor.

16. A method of electrically stimulating muscle comprising:
    delivering a first electrical muscle stimulation signal to a muscle region of the patient;
    sensing a signal indicative of a state of a tendon coupled to the muscle during the delivering step; and
    delivering a second electrical muscle stimulation signal to the muscle region with at least one signal parameter modified based on the sensed signal indicative of the state of the tendon.

17. The method of claim 16 wherein the sensing step comprises sensing a signal indicative of a change in the state of a tendon coupled to the muscle.

18. The method of claim 16 wherein the sensing step comprises sensing a signal indicative of a state of tension in the tendon coupled to the muscle.

19. The method of claim 16 wherein the sensing step comprises performing an ultrasound analysis of the tendon when delivering the first electrical muscle stimulation signal.

20. The method of claim 16 wherein the sensing step comprises sensing, at a sensing region on the body, an electrical signal that is applied to the body by an external source at a stimulation region on the body.

21. The method of claim 20 where the signal applied by the external source is applied when the muscle stimulation energy is applied to the stimulation region.

22. A system for electrical muscle stimulation, comprising:
    a first sensing pad comprising at least one electrical sensor and an anatomical marker adapted to align with a readily identifiable anatomical feature, wherein the anatomical marker allows the stimulation pad to be positioned on a patient's body in a particular location; and
    a stimulation pad comprising at least one electrical stimulation electrode,
    wherein the first sensing pad further comprises a first alignment marker that corresponds with a second alignment marker on the stimulation pad, wherein the corresponding first and second alignment markers allow a desired positioning of the stimulation pad on the user's body by aligning the first and second markers.

23. The system of claim 22 wherein the anatomical marker is an aperture.

24. The system of claim 23 wherein anatomical marker is an aperture adapted to accommodate the patient's knee.

25. The system of claim 22 wherein the first alignment marker has a first shape and the second alignment marker has a second shape, wherein the first and second shapes are complementary.

* * * * *